(12) United States Patent
Miyauchi et al.

(10) Patent No.: US 8,119,360 B2
(45) Date of Patent: Feb. 21, 2012

(54) METHOD, REAGENT AND KIT FOR DETERMINATION OF CHOLESTEROL IN REMNANT-LIKE PARTICLES (RLP)

(75) Inventors: Kazuhito Miyauchi, Shizuoka (JP); Mayumi Fujinaka, Mishima (JP)

(73) Assignee: Kyowa Medex Co., Ltd., Tokyo (JP)

( * ) Notice: Subject to any disclaimer, the term of this patent is extended or adjusted under 35 U.S.C. 154(b) by 934 days.

(21) Appl. No.: 11/815,225

(22) PCT Filed: Feb. 14, 2006

(86) PCT No.: PCT/JP2006/302528
§ 371 (c)(1),
(2), (4) Date: Aug. 1, 2007

(87) PCT Pub. No.: WO2006/085654
PCT Pub. Date: Aug. 17, 2006

(65) Prior Publication Data
US 2009/0023167 A1    Jan. 22, 2009

(30) Foreign Application Priority Data
Feb. 14, 2005 (JP) ................................. 2005-035584
Jan. 20, 2006 (JP) ................................. 2006-012767

(51) Int. Cl.
*C12Q 1/60* (2006.01)
(52) U.S. Cl. .......................................... 435/11; 435/19
(58) Field of Classification Search .................. None
See application file for complete search history.

(56) References Cited

U.S. PATENT DOCUMENTS

| 5,736,406 A | 4/1998 | Miyauchi et al. |
| 5,773,304 A | 6/1998 | Hino et al. |
| 5,807,696 A | 9/1998 | Miyauchi et al. |
| 5,888,755 A | 3/1999 | Miyauchi et al. |
| 6,794,157 B1* | 9/2004 | Sugiuchi .................... 435/11 |
| 7,202,047 B2* | 4/2007 | Miyauchi .................... 435/11 |
| 2001/0031479 A1* | 10/2001 | Miyauchi .................... 435/11 |
| 2003/0129681 A1 | 7/2003 | Kishi et al. |
| 2003/0207342 A1 | 11/2003 | Miyauchi |
| 2004/0091434 A1* | 5/2004 | Chodorowski-Kimmes et al. .............................. 424/59 |

FOREIGN PATENT DOCUMENTS

| EP | 1 132 482 | 9/2001 |
| EP | 1 148 142 | 10/2001 |
| JP | 2001231597 | 8/2001 |

OTHER PUBLICATIONS

Miyauchi, et al., "Development of homogeneous assay for measuring remnant-like particle cholesterol in serum", Clinical Chemistry, vol. 51, No. 6 Suppl. (2005) A129-30.

* cited by examiner

*Primary Examiner* — Sue Liu
*Assistant Examiner* — Satyendra Singh
(74) *Attorney, Agent, or Firm* — Fitzpatrick, Cella, Harper & Scinto

(57) ABSTRACT

The present invention provides a method, a reagent and a kit for simple and sensitive determination of cholesterol in remnant-like particles without separation of components of a sample. A method for quantitatively determining remnant-like particle cholesterol in a sample, which comprises: in an aqueous medium containing the sample and in the presence of a combination of specific surfactants and a phospholipid-hydrolyzing enzyme, allowing remnant-like particle cholesterol in the sample to react with cholesterol esterase and cholesterol oxidase or cholesterol dehydrogenase (in the presence of oxidized coenzyme); and determining the formed hydrogen peroxide or reduced coenzyme.

7 Claims, 8 Drawing Sheets

METHOD, REAGENT AND KIT FOR DETERMINATION OF CHOLESTEROL IN REMNANT-LIKE PARTICLES (RLP)

TECHNICAL FIELD

The present invention relates to a method, a reagent and a kit for quantitative determination of cholesterol in remnant-like particles (hereinafter abbreviated as RLP) considered to be a risk factor for arteriosclerosis and the like in clinical tests.

BACKGROUND ART

Blood contains various kinds of lipoproteins. These lipoproteins are classified into chylomicron (hereinafter abbreviated as CM), very low-density lipoprotein (hereinafter abbreviated as VLDL), low-density lipoprotein (hereinafter abbreviated as LDL) and high-density lipoprotein (hereinafter abbreviated as HDL) according to their specific gravity. Each class of lipoprotein has its specific ratio of constituents such as cholesterol, triglycerides, phospholipids and proteins and has a different function in vivo.

In clinical tests, cholesterol in HDL is considered as a negative risk factor for arteriosclerosis and cholesterol in LDL is considered as a positive risk factor for arteriosclerosis. Thus, the determination of cholesterol of such classes is frequently performed in the field of clinical testing.

It has been demonstrated that cholesterol in lipoproteins formed by lipid metabolism and the like is a more closely linked risk factor for arteriosclerosis than LDL cholesterol. An example of the lipoprotein formed by lipid metabolism and the like is RLP.

Recently, a method for the determination of cholesterol in RLP (hereinafter abbreviated as RLP-C) by immunoadsorption method was developed. According to this method, RLP is separated from serum by immunoaffinity chromatography using affinity gel containing anti-apoA-I monoclonal antibody and specific anti-apoB-100 monoclonal antibody which does not recognize apoB-48, and cholesterol contained in the separated RLP is determined. A reagent for the determination of cholesterol in RLP applied in this method is commercially available from JIMRO Co., Ltd. (product: RLP-cholesterol "JIMRO" II) (see non-patent document Nos. 1 and 2). This method for the determination of RLP-C by immunoadsorption method is given health insurance scores by the Ministry of Health, Labour and Welfare in Japan.

However, the above method employs affinity chromatography using antibodies and requires separation of components of a sample, which makes it a cumbersome and time-consuming method.

Also known is a simple and sensitive method for measuring RLP-C without separation of components of a sample (see patent document No. 1).
Patent document No. 1:
  Japanese Published Unexamined Patent Application No. 231597/01
Non-patent document No. 1:
  Arteriosclerosis, 25 (9, 10), 371 (1998)
Non-patent document No. 2:
  Clinical Chemistry, 48 (2), 217

DISCLOSURE OF THE INVENTION

Problems to be Solved by the Invention

An object of the present invention is to provide a method, a reagent and a kit for simple and sensitive determination of RLP-C without separation of components of a sample.

Means for Solving the Problems

The present invention has been completed based on the finding that cholesterol esterase and cholesterol oxidase or cholesterol dehydrogenase act specifically on remnant-like particle cholesterol in the presence of a combination of specific surfactants and a phospholipid-hydrolyzing enzyme. The present invention relates to the following (1) to (20).

(1) A method for quantitatively determining remnant-like particle cholesterol in a sample, which comprises: in an aqueous medium containing the sample and in the presence of (a) (i) a combination of one or more kinds of surfactants selected from the group consisting of a polyoxyethylene-polyoxybutylene copolymer, a polyoxyethylene styrenated-phenyl ether and a polyoxyethylene-polyoxypropylene long-chain branched alkyl ether [hereinafter referred to as surfactant (d1)] and one or more kinds of surfactants selected from the group consisting of a polyoxyethylene-polyoxypropylene alkylaryl ether, a polyoxyethylene alkylaryl ether, a polyoxyethylene-polyoxypropylene alkyl ether and a polyoxyethylene-polyoxypropylene short-chain branched alkyl ether [hereinafter referred to as surfactant (d2)] or (ii) a combination of a polyoxyethylene-polyoxypropylene copolymer [hereinafter referred to as surfactant (d3)] and one or two kinds of surfactants selected from the group consisting of a polyoxyethylene alkylaryl ether, a polyoxyethylene-polyoxypropylene alkyl ether and a polyoxyethylene-polyoxypropylene short-chain branched alkyl ether [hereinafter referred to as surfactant (d4)] and (b) a phospholipid-hydrolyzing enzyme, allowing (c) cholesterol esterase and cholesterol oxidase or (d) in the presence of oxidized coenzyme, cholesterol esterase and cholesterol dehydrogenase to act on remnant-like particle cholesterol in the sample to form hydrogen peroxide or reduced coenzyme; and determining the formed hydrogen peroxide or reduced coenzyme.

(2) The method according to the above (1), wherein the determination of hydrogen peroxide is carried out by allowing the formed hydrogen peroxide to react with an oxidative coloring-type chromogen in the presence of peroxidase and determining the formed dye.

(3) The method according to the above (1), wherein the determination of reduced coenzyme is carried out by measuring the absorbance of the reaction solution.

(4) The method according to the above (1), wherein the determination of reduced coenzyme is carried out by allowing the formed reduced coenzyme to react with a reductive coloring-type chromogen and determining the formed dye.

(5) The method according to any of the above (1) to (4), wherein the polyoxyethylene-polyoxybutylene copolymer is a surfactant represented by general formula (I):

$$RO\text{—}(C_2H_4O)_A\text{—}(C_4H_8O)_B\text{—}(C_2H_4O)_C\text{—}H \qquad (I)$$

(wherein A, B and C, which may be the same or different, each represent an integer of 1 to 200; and R represents a hydrogen atom, or straight-chain or branched alkyl).

(6) The method according to any of the above (1) to (5), wherein the phospholipid-hydrolyzing enzyme is phospholipase D, phospholipase C or phospholipase A2.

(7) A reagent for the quantitative determination of remnant-like particle cholesterol in a sample comprising a phospholipid-hydrolyzing enzyme, cholesterol esterase, cholesterol oxidase, and a combination of surfactant (d1) and surfactant (d2) or a combination of surfactant (d3) and surfactant (d4).

(8) The reagent according to the above (7), further comprising a reagent for the determination of hydrogen peroxide.
(9) A reagent for the quantitative determination of remnant-like particle cholesterol in a sample comprising a phospholipid-hydrolyzing enzyme, cholesterol esterase, cholesterol dehydrogenase, oxidized coenzyme, and a combination of surfactant (d1) and surfactant (d2) or a combination of surfactant (d3) and surfactant (d4).
(10) The reagent according to the above (9), further comprising a reagent for the determination of reduced coenzyme.
(11) The reagent according to any of the above (7) to (10), wherein the polyoxyethylene-polyoxybutylene copolymer is a surfactant represented by general formula (I):

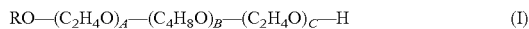

$$RO—(C_2H_4O)_A—(C_4H_8O)_B—(C_2H_4O)_C—H \quad (I)$$

(wherein A, B and C, which may be the same or different, each represent an integer of 1 to 200; and R represents a hydrogen atom, or straight-chain or branched alkyl).
(12) The reagent according to any of the above (7) to (11), wherein the phospholipid-hydrolyzing enzyme is phospholipase D, phospholipase C or phospholipase A2.
(13) A kit for the quantitative determination of remnant-like particle cholesterol in a sample which comprises a first reagent comprising surfactant (d1) and a second reagent comprising a phospholipid-hydrolyzing enzyme, cholesterol esterase and cholesterol oxidase, said kit further comprising surfactant (d2) in at least one of the first reagent and the second reagent.
(14) A kit for the quantitative determination of remnant-like particle cholesterol in a sample which comprises a first reagent comprising surfactant (d3) and a second reagent comprising a phospholipid-hydrolyzing enzyme, cholesterol esterase and cholesterol oxidase, said kit further comprising surfactant (d4) in at least one of the first reagent and the second reagent.
(15) The kit according to the above (13) or (14), further comprising a reagent for the determination of hydrogen peroxide in at least one of the first reagent and the second reagent.
(16) A kit for the quantitative determination of remnant-like particle cholesterol in a sample which comprises a first reagent comprising surfactant (d1) and a second reagent comprising a phospholipid-hydrolyzing enzyme, cholesterol esterase and cholesterol dehydrogenase, said kit further comprising surfactant (d2) in at least one of the first reagent and the second reagent, and further comprising oxidized coenzyme in at least one of the first reagent and the second reagent.
(17) A kit for the quantitative determination of remnant-like particle cholesterol in a sample which comprises a first reagent comprising surfactant (d3) and a second reagent comprising a phospholipid-hydrolyzing enzyme, cholesterol esterase and cholesterol dehydrogenase, said kit further comprising surfactant (d4) in at least one of the first reagent and the second reagent, and further comprising oxidized coenzyme in at least one of the first reagent and the second reagent.
(18) The kit according to the above (16) or (17), further comprising a reagent for the determination of reduced coenzyme in at least one of the first reagent and the second reagent.
(19) The kit according to the above (13), (15), (16) or (18), wherein the polyoxyethylene-polyoxybutylene copolymer is a surfactant represented by general formula (I):

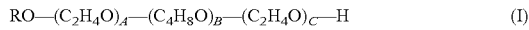

$$RO—(C_2H_4O)_A—(C_4H_8O)_B—(C_2H_4O)_C—H \quad (I)$$

(wherein A, B and C, which may be the same or different, each represent an integer of 1 to 200; and R represents a hydrogen atom, or straight-chain or branched alkyl).
(20) The kit according to any of the above (13) to (19), wherein the phospholipid-hydrolyzing enzyme is phospholipase D, phospholipase C or phospholipase A2.

Effect of the Invention

The present invention provides a method, a reagent and a kit for simple and sensitive determination of RLP-C without separation of components of a sample.

BEST MODES FOR CARRYING OUT THE INVENTION

Figure 1:
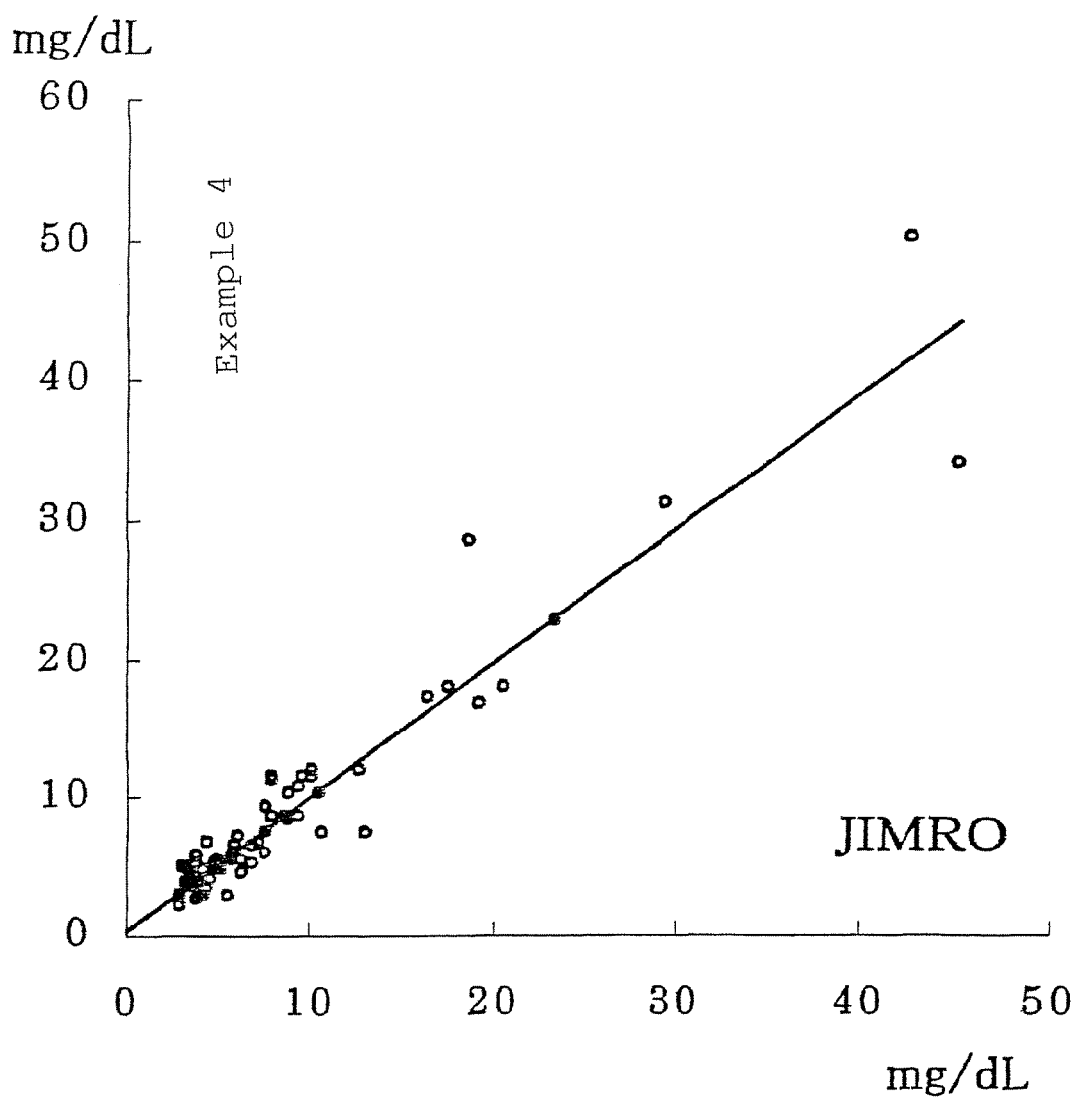
FIG. 1 is a graph showing the correlation between the determination method using RLP-cholesterol "JIMRO" II (JIMRO Co., Ltd.) and the determination method of Example 4.

In the present invention, the term "remnant-like particles (RLP)" collectively refers to VLDL remnant and CM remnant. The term "remnant-like particle cholesterol (RLP-C)" collectively refers to esterified cholesterol and free cholesterol in RLP. Accordingly, RLP-C includes esterified cholesterol in VLDL remnant, free cholesterol in VLDL remnant, esterified cholesterol in CM remnant and free cholesterol in CM remnant.
The method of the present invention can be used to determine RLP-C in samples such as whole blood, plasma and serum.
The present invention is characterized in that a combination of one or more kinds of surfactants selected from the group consisting of a polyoxyethylene-polyoxybutylene copolymer (hereinafter abbreviated as POE·POB copolymer), a polyoxyethylene styrenated-phenyl ether (hereinafter abbreviated as POE styrenated-phenyl ether) and a polyoxyethylene-polyoxypropylene long-chain branched alkyl ether (hereinafter abbreviated as POE·POP long-chain branched alkyl ether) [hereinafter referred to as surfactant (d1)] and one or more kinds of surfactants selected from the group consisting of a polyoxyethylene-polyoxypropylene alkylaryl ether (hereinafter abbreviated as POE·POP alkylaryl ether), a polyoxyethylene alkylaryl ether (hereinafter abbreviated as POE alkylaryl ether), a polyoxyethylene-polyoxypropylene alkyl ether (hereinafter abbreviated as POE·POP alkyl ether) and a polyoxyethylene-polyoxypropylene short-chain branched alkyl ether (hereinafter abbreviated as POE·POP short-chain branched alkyl ether) [hereinafter referred to as surfactant (d2)] or a combination of a polyoxyethylene-polyoxypropylene copolymer (hereinafter abbreviated as POE·POP copolymer) [hereinafter referred to as surfactant (d3)] and one or two kinds of surfactants selected from the group consisting of a polyoxyethylene alkylaryl ether (hereinafter abbreviated as POE alkylaryl ether), a polyoxyethylene-polyoxypropylene alkyl ether (hereinafter abbreviated as POE·POP alkyl ether) and a polyoxyethylene-polyoxypropylene short-chain branched alkyl ether (hereinafter abbreviated as POE·POP short-chain branched alkyl ether) [hereinafter referred to as surfactant (d4)] has an excellent effect as a surfactant for allowing enzymes used in the reactions for the determination of cholesterol to act specifically on RLP-C in the presence of a phospholipid-hydrolyzing enzyme.

That is, these combinations of surfactants allow cholesterol esterase and cholesterol oxidase or cholesterol dehydrogenase to act specifically on RLP-C in the presence of a phospholipid-hydrolyzing enzyme.

According to the present invention, RLP-C in a sample can be determined by the following steps: in an aqueous medium, in the presence of a phospholipid-hydrolyzing enzyme and in the presence of a combination of surfactants which allows cholesterol esterase and cholesterol oxidase or cholesterol dehydrogenase to act specifically on RLP-C, that is, (i) a combination of surfactant (d1) and surfactant (d2) or (ii) a combination of surfactant (d3) and surfactant (d4), allowing (c) cholesterol esterase and cholesterol oxidase or (d) in the presence of oxidized coenzyme, cholesterol esterase and cholesterol dehydrogenase to act on RLP-C in the sample to form hydrogen peroxide or reduced coenzyme; and determining the formed hydrogen peroxide or reduced coenzyme.

By allowing cholesterol esterase and cholesterol oxidase to act on RLP-C in a sample in the presence of oxygen, esterified cholesterol in RLP in the sample is converted into free cholesterol by the action of cholesterol esterase, and hydrogen peroxide is formed from the free cholesterol formed by the conversion, free cholesterol in RLP and oxygen by the action of cholesterol oxidase.

By allowing cholesterol esterase and cholesterol dehydrogenase to act on RLP-C in a sample in the presence of oxidized coenzyme, esterified cholesterol in RLP in the sample is converted into free cholesterol by the action of cholesterol esterase, and reduced coenzyme is formed from the free cholesterol formed by the conversion, free cholesterol in RLP and oxidized coenzyme by the action of cholesterol dehydrogenase.

The enzymatic reactions are carried out in an aqueous solution such as a buffer containing cholesterol esterase and cholesterol oxidase or cholesterol dehydrogenase which are necessary for the determination of cholesterol (oxidized coenzyme is necessary when cholesterol dehydrogenase is used) in the presence of a combination of surfactant (d1) and surfactant (d2) or a combination of surfactant (d3) and surfactant (d4) and a phospholipid-hydrolyzing enzyme.

In the combination of surfactant (d1) and surfactant (d2) and the combination of surfactant (d3) and surfactant (d4), one or more kinds of surfactants constituting surfactants (d1) to (d4) may be used as surfactant (d1), surfactant (d2), surfactant (d3) and surfactant (d4).

Examples of combinations of surfactant (d1) and surfactant (d2) are shown in Tables 1 to 7.

TABLE 1

| Surfactant (d1) | Surfactant (d2) |
| --- | --- |
| POE•POB copolymer | POE•POP alkylaryl ether |
| POE•POB copolymer | POE alkylaryl ether |
| POE•POB copolymer | POE•POP alkyl ether |
| POE•POB copolymer | POE•POP short-chain branched alkyl ether |
| POE•POB copolymer | POE•POP alkylaryl ether |
|  | POE alkylaryl ether |
| POE•POB copolymer | POE•POP alkylaryl ether |
|  | POE•POP alkyl ether |
| POE•POB copolymer | POE•POP alkylaryl ether |
|  | POE•POP short-chain branched alkyl ether |
| POE•POB copolymer | POE alkylaryl ether |
|  | POE•POP alkyl ether |
| POE•POB copolymer | POE alkylaryl ether |
|  | POE•POP short-chain branched alkyl ether |
| POE•POB copolymer | POE•POP alkyl ether |
|  | POE•POP short-chain branched alkyl ether |
| POE•POB copolymer | POE•POP alkylaryl ether |
|  | POE alkylaryl ether |
|  | POE•POP alkyl ether |
| POE•POB copolymer | POE•POP alkylaryl ether |
|  | POE alkylaryl ether |
|  | POE•POP short-chain branched alkyl ether |
| POE•POB copolymer | POE•POP alkylaryl ether |
|  | POE•POP alkyl ether |
|  | POE•POP short-chain branched alkyl ether |
| POE•POB copolymer | POE alkylaryl ether |
|  | POE•POP alkyl ether |
|  | POE•POP short-chain branched alkyl ether |
| POE•POB copolymer | POE•POP alkylaryl ether |
|  | POE alkylaryl ether |
|  | POE•POP alkyl ether |
|  | POE•POP short-chain branched alkyl ether |

TABLE 2

| Surfactant (d1) | Surfactant (d2) |
| --- | --- |
| POE styrenated-phenyl ether | POE•POP alkylaryl ether |
| POE styrenated-phenyl ether | POE alkylaryl ether |
| POE styrenated-phenyl ether | POE•POP alkyl ether |
| POE styrenated-phenyl ether | POE•POP short-chain branched alkyl ether |
| POE styrenated-phenyl ether | POE•POP alkylaryl ether |
|  | POE alkylaryl ether |
| POE styrenated-phenyl ether | POE•POP alkylaryl ether |
|  | POE•POP alkyl ether |
| POE styrenated-phenyl ether | POE•POP alkylaryl ether |
|  | POE•POP short-chain branched alkyl ether |
| POE styrenated-phenyl ether | POE alkylaryl ether |
|  | POE•POP alkyl ether |
| POE styrenated-phenyl ether | POE alkylaryl ether |
|  | POE•POP short-chain branched alkyl ether |
| POE styrenated-phenyl ether | POE•POP alkyl ether |
|  | POE•POP short-chain branched alkyl ether |
| POE styrenated-phenyl ether | POE•POP alkylaryl ether |
|  | POE alkylaryl ether |
|  | POE•POP alkyl ether |
| POE styrenated-phenyl ether | POE•POP alkylaryl ether |
|  | POE alkylaryl ether |
|  | POE•POP short-chain branched alkyl ether |

TABLE 2-continued

| Surfactant (d1) | Surfactant (d2) |
| --- | --- |
| POE styrenated-phenyl ether | POE•POP alkylaryl ether<br>POE•POP alkyl ether<br>POE•POP short-chain branched alkyl ether |
| POE styrenated-phenyl ether | POE alkylaryl ether<br>POE•POP alkyl ether<br>POE•POP short-chain branched alkyl ether |
| POE styrenated-phenyl ether | POE•POP alkylaryl ether<br>POE alkylaryl ether<br>POE•POP alkyl ether<br>POE•POP short-chain branched alkyl ether |

TABLE 3

| Surfactant (d1) | Surfactant (d2) |
| --- | --- |
| POE•POP long-chain branched alkyl ether | POE•POP alkylaryl ether |
| POE•POP long-chain branched alkyl ether | POE alkylaryl ether |
| POE•POP long-chain branched alkyl ether | POE•POP alkyl ether |
| POE•POP long-chain branched alkyl ether | POE•POP short-chain branched alkyl ether |
| POE•POP long-chain branched alkyl ether | POE•POP alkylaryl ether<br>POE alkylaryl ether |
| POE•POP long-chain branched alkyl ether | POE•POP alkylaryl ether<br>POE•POP alkyl ether |
| POE•POP long-chain branched alkyl ether | POE•POP alkylaryl ether<br>POE•POP short-chain branched alkyl ether |
| POE•POP long-chain branched alkyl ether | POE alkylaryl ether<br>POE•POP alkyl ether |
| POE•POP long-chain branched alkyl ether | POE alkylaryl ether<br>POE•POP short-chain branched alkyl ether |
| POE•POP long-chain branched alkyl ether | POE•POP alkyl ether<br>POE•POP short-chain branched alkyl ether |
| POE•POP long-chain branched alkyl ether | POE•POP alkylaryl ether<br>POE alkylaryl ether<br>POE•POP alkyl ether |
| POE•POP long-chain branched alkyl ether | POE•POP alkylaryl ether<br>POE alkylaryl ether<br>POE•POP short-chain branched alkyl ether |
| POE•POP long-chain branched alkyl ether | POE•POP alkylaryl ether<br>POE•POP alkyl ether<br>POE•POP short-chain branched alkyl ether |
| POE•POP long-chain branched alkyl ether | POE alkylaryl ether<br>POE•POP alkyl ether<br>POE•POP short-chain branched alkyl ether |
| POE•POP long-chain branched alkyl ether | POE•POP alkylaryl ether<br>POE alkylaryl ether<br>POE•POP alkyl ether<br>POE•POP short-chain branched alkyl ether |

TABLE 4

| Surfactant (d1) | Surfactant (d2) |
| --- | --- |
| POE•POB copolymer<br>POE styrenated-phenyl ether | POE•POP alkylaryl ether |
| POE•POB copolymer<br>POE styrenated-phenyl ether | POE alkylaryl ether |
| POE•POB copolymer<br>POE styrenated-phenyl ether | POE•POP alkyl ether |
| POE•POB copolymer<br>POE styrenated-phenyl ether | POE•POP short-chain branched alkyl ether |
| POE•POB copolymer<br>POE styrenated-phenyl ether | POE•POP alkylaryl ether<br>POE alkylaryl ether |
| POE•POB copolymer<br>POE styrenated-phenyl ether | POE•POP alkylaryl ether<br>POE•POP alkyl ether |
| POE•POB copolymer<br>POE styrenated-phenyl ether | POE•POP alkylaryl ether<br>POE•POP short-chain branched alkyl ether |
| POE•POB copolymer<br>POE styrenated-phenyl ether | POE alkylaryl ether<br>POE•POP alkyl ether |
| POE•POB copolymer<br>POE styrenated-phenyl ether | POE alkylaryl ether<br>POE•POP short-chain branched alkyl ether |
| POE•POB copolymer<br>POE styrenated-phenyl ether | POE•POP alkyl ether<br>POE•POP short-chain branched alkyl ether |
| POE•POB copolymer<br>POE styrenated-phenyl ether | POE•POP alkylaryl ether<br>POE alkylaryl ether<br>POE•POP alkyl ether |
| POE•POB copolymer<br>POE styrenated-phenyl ether | POE•POP alkylaryl ether<br>POE alkylaryl ether<br>POE•POP short-chain branched alkyl ether |
| POE•POB copolymer<br>POE styrenated-phenyl ether | POE•POP alkylaryl ether<br>POE•POP alkyl ether<br>POE•POP short-chain branched alkyl ether |
| POE•POB copolymer<br>POE styrenated-phenyl ether | POE alkylaryl ether<br>POE•POP alkyl ether<br>POE•POP short-chain branched alkyl ether |
| POE•POB copolymer<br>POE styrenated-phenyl ether | POE•POP alkylaryl ether<br>POE alkylaryl ether<br>POE•POP alkyl ether<br>POE•POP short-chain branched alkyl ether |

TABLE 5

| Surfactant (d1) | Surfactant (d2) |
| --- | --- |
| POE•POB copolymer<br>POE•POP long-chain branched alkyl ether | POE•POP alkylaryl ether |
| POE•POB copolymer<br>POE•POP long-chain branched alkyl ether | POE alkylaryl ether |
| POE•POB copolymer<br>POE•POP long-chain branched alkyl ether | POE•POP alkyl ether |
| POE•POB copolymer<br>POE•POP long-chain branched alkyl ether | POE•POP short-chain branched alkyl ether |
| POE•POB copolymer<br>POE•POP long-chain branched alkyl ether | POE•POP alkylaryl ether<br>POE alkylaryl ether |
| POE•POB copolymer<br>POE•POP long-chain branched alkyl ether | POE•POP alkylaryl ether<br>POE•POP alkyl ether |
| POE•POB copolymer<br>POE•POP long-chain branched alkyl ether | POE•POP alkylaryl ether<br>POE•POP short-chain branched alkyl ether |
| POE•POB copolymer<br>POE•POP long-chain branched alkyl ether | POE alkylaryl ether<br>POE•POP alkyl ether |
| POE•POB copolymer<br>POE•POP long-chain branched alkyl ether | POE alkylaryl ether<br>POE•POP short-chain branched alkyl ether |
| POE•POB copolymer<br>POE•POP long-chain branched alkyl ether | POE•POP alkyl ether<br>POE•POP short-chain branched alkyl ether |
| POE•POB copolymer<br>POE•POP long-chain branched alkyl ether | POE•POP alkylaryl ether<br>POE alkylaryl ether<br>POE•POP alkyl ether |

TABLE 5-continued

| Surfactant (d1) | Surfactant (d2) |
|---|---|
| POE•POB copolymer<br>POE•POP long-chain branched alkyl ether | POE•POP alkylaryl ether<br>POE alkylaryl ether<br>POE•POP short-chain branched alkyl ether |
| POE•POB copolymer<br>POE•POP long-chain branched alkyl ether | POE•POP alkylaryl ether<br>POE•POP alkyl ether<br>POE•POP short-chain branched alkyl ether |
| POE•POB copolymer<br>POE•POP long-chain branched alkyl ether | POE alkylaryl ether<br>POE•POP alkyl ether<br>POE•POP short-chain branched alkyl ether |
| POE•POB copolymer<br>POE•POP long-chain branched alkyl ether | POE•POP alkylaryl ether<br>POE alkylaryl ether<br>POE•POP alkyl ether<br>POE•POP short-chain branched alkyl ether |

TABLE 6

| Surfactant (d1) | Surfactant (d2) |
|---|---|
| POE styrenated-phenyl ether<br>POE•POP long-chain branched alkyl ether | POE•POP alkylaryl ether |
| POE styrenated-phenyl ether<br>POE•POP long-chain branched alkyl ether | POE alkylaryl ether |
| POE styrenated-phenyl ether<br>POE•POP long-chain branched alkyl ether | POE•POP alkyl ether |
| POE styrenated-phenyl ether<br>POE•POP long-chain branched alkyl ether | POE•POP short-chain branched alkyl ether |
| POE styrenated-phenyl ether<br>POE•POP long-chain branched alkyl ether | POE•POP alkylaryl ether<br>POE alkylaryl ether |
| POE styrenated-phenyl ether<br>POE•POP long-chain branched alkyl ether | POE•POP alkylaryl ether<br>POE•POP alkyl ether |
| POE styrenated-phenyl ether<br>POE•POP long-chain branched alkyl ether | POE•POP alkylaryl ether<br>POE•POP short-chain branched alkyl ether |
| POE styrenated-phenyl ether<br>POE•POP long-chain branched alkyl ether | POE alkylaryl ether<br>POE•POP alkyl ether |
| POE styrenated-phenyl ether<br>POE•POP long-chain branched alkyl ether | POE alkylaryl ether<br>POE•POP short-chain branched alkyl ether |
| POE styrenated-phenyl ether<br>POE•POP long-chain branched alkyl ether | POE•POP alkyl ether<br>POE•POP short-chain branched alkyl ether |
| POE styrenated-phenyl ether<br>POE•POP long-chain branched alkyl ether | POE•POP alkylaryl ether<br>POE alkylaryl ether<br>POE•POP alkyl ether |
| POE styrenated-phenyl ether<br>POE•POP long-chain branched alkyl ether | POE•POP alkylaryl ether<br>POE•POP alkyl ether<br>POE•POP short-chain branched alkyl ether |
| POE styrenated-phenyl ether<br>POE•POP long-chain branched alkyl ether | POE•POP alkylaryl ether<br>POE alkylaryl ether<br>POE•POP short-chain branched alkyl ether |
| POE styrenated-phenyl ether<br>POE•POP long-chain branched alkyl ether | POE alkylaryl ether<br>POE•POP alkyl ether<br>POE•POP short-chain branched alkyl ether |
| POE styrenated-phenyl ether<br>POE•POP long-chain branched alkyl ether | POE•POP alkylaryl ether<br>POE alkylaryl ether<br>POE•POP alkyl ether<br>POE•POP short-chain branched alkyl ether |

TABLE 7

| Surfactant (d1) | Surfactant (d2) |
|---|---|
| POE•POB copolymer<br>POE styrenated-phenyl ether<br>POE•POP long-chain branched alkyl ether | POE•POP alkylaryl ether |
| POE•POB copolymer<br>POE styrenated-phenyl ether<br>POE•POP long-chain branched alkyl ether | POE alkylaryl ether |
| POE•POB copolymer<br>POE styrenated-phenyl ether<br>POE•POP long-chain branched alkyl ether | POE•POP alkyl ether |
| POE•POB copolymer<br>POE styrenated-phenyl ether<br>POE•POP long-chain branched alkyl ether | POE•POB short-chain branched alkyl ether |
| POE•POB copolymer<br>POE styrenated-phenyl ether<br>POE•POP long-chain branched alkyl ether | POE•POP alkylaryl ether<br>POE alkylaryl ether |
| POE•POB copolymer<br>POE styrenated-phenyl ether<br>POE•POP long-chain branched alkyl ether | POE•POP alkylaryl ether<br>POE•POP alkyl ether |
| POE•POB copolymer<br>POE styrenated-phenyl ether<br>POE•POP long-chain branched alkyl ether | POE•POP alkylaryl ether<br>POE•POP short-chain branched alkyl ether |
| POE•POB copolymer<br>POE styrenated-phenyl ether<br>POE•POP long-chain branched alkyl ether | POE alkylaryl ether<br>POE•POP alkyl ether |
| POE•POB copolymer<br>POE styrenated-phenyl ether<br>POE•POP long-chain branched alkyl ether | POE alkylaryl ether<br>POE•POP short-chain branched alkyl ether |
| POE•POB copolymer<br>POE styrenated-phenyl ether<br>POE•POP long-chain branched alkyl ether | POE•POP alkyl ether<br>POE•POP short-chain branched alkyl ether |
| POE•POB copolymer<br>POE styrenated-phenyl ether<br>POE•POP long-chain branched alkyl ether | POE•POP alkylaryl ether<br>POE alkylaryl ether<br>POE•POP alkyl ether |
| POE•POB copolymer<br>POE styrenated-phenyl ether<br>POE•POP long-chain branched alkyl ether | POE•POP alkylaryl ether<br>POE•POP alkyl ether<br>POE•POP short-chain branched alkyl ether |
| POE•POB copolymer<br>POE styrenated-phenyl ether<br>POE•POP long-chain branched alkyl ether | POE•POP alkylaryl ether<br>POE alkylaryl ether<br>POE•POP short-chain branched alkyl ether |
| POE•POB copolymer<br>POE styrenated-phenyl ether<br>POE•POP long-chain branched alkyl ether | POE alkylaryl ether<br>POE•POP alkyl ether<br>POE•POP short-chain branched alkyl ether |
| POE•POB copolymer<br>POE styrenated-phenyl ether<br>POE•POP long-chain branched alkyl ether | POE•POP alkylaryl ether<br>POE alkylaryl ether<br>POE•POP alkyl ether<br>POE•POP short-chain branched alkyl ether |

Among the combinations of surfactant (d1) and surfactant (d2), preferred are combinations with a strong effect of allowing cholesterol esterase and cholesterol oxidase or cholesterol dehydrogenase to act specifically on remnant-like particle cholesterol in the presence of a phospholipid-hydrolyzing enzyme.

Specifically, combinations of POE·POB copolymer and surfactant (d2) shown in Table 1 are preferred.

Among the combinations of POE·POB copolymer and surfactant (d2), more preferred are combinations shown below in Table 8.

TABLE 8

| Surfactant (d1) | Surfactant (d2) |
| --- | --- |
| POE•POB copolymer | POE•POP alkylaryl ether |
| POE•POB copolymer | POE•POP alkyl ether |
| POE•POB copolymer | POE•POP short-chain branched alkyl ether |
| POE•POB copolymer | POE•POP alkylaryl ether |
| | POE•POP alkyl ether |
| POE•POB copolymer | POE•POP alkylaryl ether |
| | POE•POP short-chain branched alkyl ether |
| POE•POB copolymer | POE•POP alkyl ether |
| | POE•POP short-chain branched alkyl ether |
| POE•POB copolymer | POE•POP alkylaryl ether |
| | POE•POP alkyl ether |
| | POE•POP short-chain branched alkyl ether |

Examples of combinations of surfactant (d3) and surfactant (d4) are shown in Table 9 below.

TABLE 9

| Surfactant (d3) | Surfactant (d4) |
| --- | --- |
| POE•POP copolymer | POE alkylaryl ether |
| POE•POP copolymer | POE•POP alkyl ether |
| POE•POP copolymer | POE•POP short-chain branched alkyl ether |
| POE•POP copolymer | POE alkylaryl ether |
| | POE•POP alkyl ether |
| POE•POP copolymer | POE alkylaryl ether |
| | POE•POP short-chain branched alkyl ether |
| POE•POP copolymer | POE•POP alkyl ether |
| | POE•POP short-chain branched alkyl ether |
| POE•POP copolymer | POE alkylaryl ether |
| | POE•POP alkyl ether |
| | POE•POP short-chain branched alkyl ether |

Among the combinations of surfactant (d3) and surfactant (d4), preferred are combinations with a strong effect of allowing cholesterol esterase and cholesterol oxidase or cholesterol dehydrogenase to act specifically on RLP-C in the presence of a phospholipid-hydrolyzing enzyme.

Specifically, combinations shown below in Table 10 are preferred.

TABLE 10

| Surfactant (d3) | Surfactant (d4) |
| --- | --- |
| POE•POP copolymer | POE•POP alkyl ether |
| POE•POP copolymer | POE•POP short-chain branched alkyl ether |
| POE•POP copolymer | POE alkylaryl ether |
| | POE•POP alkyl ether |
| POE•POP copolymer | POE alkylaryl ether |
| | POE•POP short-chain branched alkyl ether |
| POE•POP copolymer | POE•POP alkyl ether |
| | POE•POP short-chain branched alkyl ether |

Determination of hydrogen peroxide or reduced coenzyme formed by the reactions is carried out by a method known per se.

If necessary, the enzymatic reactions may be carried out in the presence of cyclodextrin or its derivative, albumin or a lipoprotein aggregating agent. The use of cyclodextrin or its derivative, albumin or a lipoprotein aggregating agent is preferable because it can inhibit the enzymes from acting on cholesterol in lipoproteins other than remnant-like particles.

The reaction solution for enzymatic reactions may further contain, if necessary, an enzyme activator that is generally used to activate cholesterol esterase and cholesterol oxidase or cholesterol dehydrogenase, a stabilizer, an antiseptic, an interference inhibitor and various kinds of salts for solubilizing proteins such as globulin in a biological sample, as far as they do not affect the specificity of the reaction for determination of RLP-C.

The reaction for cholesterol ester hydrolysis and the reaction for oxidation or dehydrogenation of free cholesterol can be carried out successively in the presence of a phospholipid-hydrolyzing enzyme and a combination of surfactant (d1) and surfactant (d2) or a combination of surfactant (d3) and surfactant (d4). The reactions of cholesterol may be carried out by first contacting a sample with the surfactants in an aqueous solution and then adding thereto the phospholipid-hydrolyzing enzyme and the enzymes concerned in the reactions of cholesterol. The reactions of cholesterol may be carried out in an aqueous solution containing all the components necessary for the determination of RLP-C or may be carried out by dividing the components necessary for the determination of RLP-C into two or three groups and then adding successively the groups of components to the reaction solution. Determination of RLP-C is preferably carried out by using a kit for the determination of RLP-C described below.

In the aqueous medium, cholesterol esterase, cholesterol oxidase and cholesterol dehydrogenase are used usually at a concentration of 0.001 to 400 U/mL, preferably 0.01 to 200 U/mL, more preferably 0.05 to 100 U/mL.

The concentration of the phospholipid-hydrolyzing enzyme in the aqueous medium is not specifically limited, but is preferably 0.001 to 400 U/mL, more preferably 0.01 to 200 U/mL, and particularly preferably 0.05 to 100 U/mL.

In the aqueous medium, the concentration of each of surfactant (d1), surfactant (d2), surfactant (d3) and surfactant (d4) is preferably 0.001 to 5 (w/v) %, more preferably 0.005 to 2.5 (w/v) %, and particularly preferably 0.05 to 1 (w/v) %.

The enzymatic reactions are carried out usually at 10 to 50° C., preferably 20 to 40° C., and completed generally in 2 to 30 minutes.

The formed hydrogen peroxide is determined, for example, by subjecting the hydrogen peroxide to reaction with a chromogen which is converted into a dye by hydrogen peroxide and oxidation in the presence of peroxidase to form a dye, and measuring the change in the absorbance of the reaction solution, for example, at the absorption maximum wavelength of the formed dye. The hydrogen peroxide is also determined, for example, by subjecting it to reaction with a chemiluminescent substance such as luminol, isoluminol, lucigenin or acridinium ester to form photon, and determining the formed photon.

The reduced coenzyme can be determined, for example, by measuring the absorbance of a solution containing the reduced coenzyme formed by the enzymatic reactions at 300 to 500 nm, preferably 330 to 400 nm, more preferably around 340 nm. The reduced coenzyme can also be determined, for example, by subjecting the reduced coenzyme to reaction with a chromogen which is converted into a dye by reduced coenzyme and reduction in the presence of diaphorase or an electron carrier to form a dye, and measuring the change in the absorbance of the reaction solution, for example, at the absorption maximum wavelength of the formed dye. An example of the electron carrier is 1-methoxy-5-methylphenazium methylsulfate.

The concentration of RLP-C in a sample can be calculated from a calibration curve showing the relationship between the cholesterol concentration and the amount of hydrogen peroxide or reduced coenzyme previously prepared using samples containing RLP-C at known concentrations.

As the cholesterol esterase, enzymes that can hydrolyze cholesterol ester, for example, cholesterol esterase and lipoprotein lipase are used. They may be obtained from animals, plants or microorganisms, or produced by genetic engineering techniques, and chemically modified ones can also be used. Examples of the chemically modified enzymes include enzymes that are modified with chemically modifying groups such as a group comprising polyethylene glycol or polypropylene glycol as a main component, a group having a copolymer of polypropylene glycol and polyethylene glycol, a group comprising a water-soluble polysaccharide, a sulfopropyl group, a sulfobutyl group, a polyurethane group and a group having the chelating function. Specifically preferred is an enzyme modified with a group comprising polyethylene glycol as a main component. Examples of the water-soluble polysaccharides include dextran, pullulan and soluble starch.

Examples of reagents for chemical modification (chemical modifiers) include compounds that have both the above chemically modifying group and a functional group or a structure which can react with an amino group, a carboxyl group, a sulfhydryl group or the like of an enzyme. Examples of the functional groups or structures which can react with an amino group of an enzyme include a carboxyl group, an activated ester group (e.g., N-hydroxysuccinimide group), an acid anhydride, an acid chloride, an aldehyde, an epoxide group, 1,3-propanesultone and 1,4-butanesultone. An example of the functional group or structure which can react with a carboxyl group of an enzyme is an amino group. Examples of the groups or structures reactive with a sulfhydryl group of an enzyme include a maleimide group, a disulfide and α-haloester (e.g., α-iodo ester).

Examples of the chemical modifiers are Sunbright VFM-4101, Sunbright MEAC-50HS and Sunbright MEC-50HS which have a group comprising polyethylene glycol as a main component and an N-hydroxysuccinimide group (all produced by NOF Corporation), Sunbright AKM series (e.g., Sunbright AKM-1510), Sunbright ADM series and Sunbright ACM series which have a group comprising polyalkylene glycol as a main component and an acid anhydride structure (all produced by NOF Corporation), EPOX-3400 and M-EPOX-5000 which have a group comprising polyethylene glycol as a main component and an epoxide group (both produced by Sheawater Polymers), diethylenetriamine-N,N, N',N'',N''-pentaacetic anhydride which has a group having the chelating function and an acid anhydride structure (DTPA anhydride, Dojindo Laboratories), activated polyurethane P4000 for polyurethane modification (Boehringer Mannheim), dextran T40 for dextran modification and activated TCT (Boehringer Mannheim).

Chemical modification of an enzyme can be carried out, for example, in the following manner.

Cholesterol esterase is dissolved in a buffer of pH 8.0 or higher such as HEPES buffer, and 0.01 to 500-fold molar amount of a chemical modifier is added thereto at 0 to 55° C., followed by stirring for 5 minutes to 5 hours. In the actual enzymatic reaction, this reaction mixture can be used as such, or if necessary, after removal of the unreacted chemical modifier with an ultrafilter, as the chemically modified cholesterol esterase.

The cholesterol oxidase used in the method may be obtained from animals, plants or microorganisms, or produced by genetic engineering techniques, and chemically modified ones can also be used.

The chemically modified enzymes can be prepared by the above method for chemical modification.

As the cholesterol dehydrogenase, any enzymes having the ability to form reduced coenzyme by oxidizing cholesterol in the presence of oxidized coenzyme can be used. They may be obtained from animals, plants or microorganisms, or produced by genetic engineering techniques, and chemically modified ones can also be used. The chemically modified enzymes can be prepared, for example, by the above method for chemical modification using the above chemical modifier.

As to the phospholipid-hydrolyzing enzyme, there is not any specific restriction so long as it is an enzyme having the ability to hydrolyze phospholipids. For example, phospholipid-hydrolyzing enzymes obtained from animals, plants and microorganisms can be employed. Specific examples of the phospholipid-hydrolyzing enzymes are phospholipase D, phospholipase C, phospholipase A2 and lysophospholipase.

Examples of the oxidized coenzymes used in the present method for the determination using cholesterol dehydrogenase are NAD, NADP, thio-NAD and thio-NADP.

Surfactant (d1) used in the present invention has the function to allow cholesterol esterase and cholesterol oxidase or cholesterol dehydrogenase to act specifically on RLP-C in the presence of a phospholipid-hydrolyzing enzyme when used in combination with surfactant (d2) used in the present invention. Each of surfactant (d1) and surfactant (d2) does not necessarily need to have a high function to allow cholesterol esterase and cholesterol oxidase or cholesterol dehydrogenase to act specifically on RLP-C when used alone.

Surfactant (d3) used in the present invention has the function to allow cholesterol esterase and cholesterol oxidase or cholesterol dehydrogenase to act specifically on RLP-C in the presence of a phospholipid-hydrolyzing enzyme when used in combination with surfactant (d4) used in the present invention. Each of surfactant (d3) and surfactant (d4) does not necessarily need to have a high function to allow cholesterol esterase and cholesterol oxidase or cholesterol dehydrogenase to act specifically on RLP-C when used alone.

The POE·POB copolymer includes random polymers and block polymers of polyoxyethylene and polyoxybutylene, for example, compounds represented by general formula (I):

$$RO-(C_2H_4O)_A-(C_4H_8O)_B-(C_2H_4O)_C-H \qquad (I)$$

(wherein A, B and C, which may be the same or different, each represent an integer of 1 to 200; and R represents a hydrogen atom, or straight-chain or branched alkyl) [hereinafter referred to as Compound (I)]. It is preferred that R in general formula (I) is a hydrogen atom.

The straight-chain or branched alkyl in Compound (I) includes alkyl groups having 1 to 30 carbon atoms, such as methyl, ethyl, propyl, isopropyl, butyl, isobutyl, sec-butyl, tert-butyl, pentyl, isopentyl, neopentyl, hexyl, isohexyl, heptyl, isoheptyl, octyl, isooctyl, nonyl, isononyl, decyl, isodecyl, undecyl, isoundecyl, dodecyl, isododecyl, tridecyl, isotridecyl, tetradecyl, isotetradecyl, pentadecyl, isopentadecyl, hexadecyl, isohexadecyl, heptadecyl, isoheptadecyl, octadecyl, isooctadecyl, nonadecyl, isononadecyl, icosyl, isoicosyl, heneicosyl, isoheneicosyl, docosyl (behenyl), isodoecosyl, tricosyl, isotricosyl, tetracosyl, isotetracosyl, pentacosyl, isopentacosyl, hexacosyl, isohexacosyl, heptacosyl, isoheptacosyl, octacosyl, isooctacosyl, nonacosyl, isononacosyl, triacontyl and isotriacontyl.

The molecular weight of the polyoxybutylene moiety is preferably 700 or more, more preferably 1,000 or more, and particularly preferably 1,500 or more.

Specific examples of Compound (I) include Plonon B-204 and Plonon B-208 (both produced by NOF Corporation).

Examples of the POE styrenated-phenyl ether are BLAUNON DSP-9, BLAUNON DSP-12.5, BLAUNON DSP-20, BLAUNON DSP-10, BLAUNON TSP-5, BLAUNON TSP-7.5, BLAUNON TSP-16, BLAUNON TSP-20 and BLAUNON TSP-50 (all produced by Aoki Oil Industrial Co., Ltd.), which are commercially available.

The long-chain branched alkyl in the POE·POP long-chain branched alkyl ether includes, for example, branched alkyl groups having 20 to 30 carbon atoms, such as isoicosyl, octyldodecyl, isoheneicosyl, isodoecosyl, isotricosyl, isotetracosyl, decyltetradecyl, isopentacosyl, isohexacosyl, dodecyltetradecyl, isoheptacosyl, isooctacosyl, isononacosyl and isotriacontyl. An example of the POE·POP long-chain branched alkyl ether is UNILUB MT-0620B (produced by NOF Corporation), which is commercially available.

The alkyl in the POE·POP alkylaryl ether and the POE alkylaryl ether includes, for example, alkyl groups having 8 or more carbon atoms, such as octyl and nonyl. The aryl in the POE·POP alkylaryl ether and the POE alkylaryl ether includes, for example, phenyl and naphthyl. Phenyl is preferred as the aryl.

The alkyl in the POE·POP alkyl ether includes alkyl groups having 6 to 30 carbon atoms, such as hexyl, heptyl, octyl, nonyl, decyl, undecyl, dodecyl (lauryl), tridecyl, tetradecyl (myristyl), pentadecyl, hexadecyl (cetyl), heptadecyl, octadecyl (stearyl), nonadecyl, icosyl, heneicosyl, docosyl (behenyl), tricosyl, tetracosyl, pentacosyl, hexacosyl, heptacosyl, octacosyl, nonacosyl and triacontyl.

The short-chain branched alkyl in the POE·POP short-chain branched alkyl ether includes branched alkyl groups having 6 to 19 carbon atoms, such as isohexyl, isoheptyl, isooctyl, isononyl, isodecyl, isoundecyl, isododecyl, isotridecyl, isotetradecyl, isopentadecyl, isohexadecyl, isoheptadecyl, isooctadecyl and isononadecyl.

An example of the POE·POP alkylaryl ether is polyoxyethylene-polyoxypropylene alkylphenyl ether. Specific examples include Emulgen L-40 (produced by Kao Corporation) and Acronecess KP-189R (produced by NOF Corporation), which are commercially available.

An example of the POE alkylaryl ether is polyoxyethylene alkylphenyl ether. Specific examples include Emulgen 911 and Emulgen 810 (produced by Kao Corporation), and Nonion HS-210, Nonion HS-215, Nonion NS-208.5 and Nonion HS-208 (all produced by NOF Corporation), which are commercially available.

As the POE·POP alkyl ether and the POE·POP branched alkyl ether, those with a hydrophile-lipophile balance (HLB) of 9 to 20 are preferred. Specific examples of the POE·POP alkyl ether include Wondersurf RL-100 and Wondersurf S-1000 (both produced by Aoki Oil Industrial Co., Ltd.), which are commercially available. Specific examples of the POE·POP short-chain branched alkyl ether include Wondersurf ID-70 and Wondersurf ID-90 (both produced by Aoki Oil Industrial Co., Ltd.), which are commercially available.

The POE·POP copolymer includes random polymers and block polymers of polyoxyethylene and polyoxypropylene, for example, compounds represented by general formula (II):

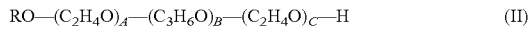

$$\text{RO}-(C_2H_4O)_A-(C_3H_6O)_B-(C_2H_4O)_C-H \quad \text{(II)}$$

(wherein A, B and C, which may be the same or different, each represent an integer of 1 to 200; and R represents a hydrogen atom, or straight-chain or branched alkyl). It is preferred that R in general formula (II) is a hydrogen atom.

The straight-chain or branched alkyl in Compound (II) includes the same alkyl groups as those in Compound (I) mentioned above.

The molecular weight of the polyoxypropylene moiety of the compound is preferably 2,050 or more, more preferably 2,750 or more, and particularly preferably 3,250 or more.

Specific examples include Pluronic F-108, Pluronic L-121, Pluronic L-122, Pluronic L-101 and Pluronic L-103 (all produced by Adeka Corporation), and Plonon 102, Plonon 104, Plonon 201, Plonon 204, Plonon 208 and Plonon 202B (all produced by NOF Corporation), which are commercially available.

Examples of the aqueous media include deionized water, distilled water and a buffer solution, and preferred is a buffer solution. Examples of the buffers used in the buffer solution include tris(hydroxymethyl)aminomethane buffer, phosphate buffer, borate buffer and Good's buffer.

Examples of Good's buffer include 2-morpholinoethanesulfonic acid (MES), bis(2-hydroxyethyl)iminotris(hydroxymethyl)methane (Bis-Tris), N-(2-acetamido)iminodiacetic acid (ADA), piperazine-N,N'-bis(2-ethanesulfonic acid) (PIPES), N-(2-acetamido)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[tris(hydroxymethyl)methyl]glycine (Tricine), N,N-bis(2-hydroxyethyl)glycine (Bicine), N-tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO) and N-cyclohexyl-3-aminopropanesulfonic acid (CAPS).

The pH of the buffer solution is usually 4 to 10, preferably 5 to 9, and the concentration of the buffer solution is usually 0.001 to 0.5 mol/L, preferably 0.005 to 0.2 mol/L, more preferably 0.01 to 0.1 mol/L.

The chromogens used for the determination of hydrogen peroxide are, for example, those which are converted into a dye by hydrogen peroxide and oxidation in the presence of peroxidase. Examples of the chromogens include leuco-type chromogens and oxidative coupling-type chromogens. A leuco-type chromogen is a substance that is converted into a dye by itself in the presence of hydrogen peroxide and a peroxidative substance such as peroxidase.

Examples of the leuco-type chromogens are 10-N-carboxymethylcarbamoyl-3,7-bis(dimethylamino)-10H-phenothiazine (CCAP), 10-(N-methylcarbamoyl)-3,7-bis(dimethylamino)-10H-phenothiazine (MCDP), N-(carboxymethylaminocarbonyl)-4,4'-bis(dimethylamino)diphenylamine sodium salt (DA-64), 4,4'-bis(dimethylamino)diphenylamine and bis[3-bis(4-chlorophenyl)methyl-4-dimethylaminophenyl]amine (BCMA).

An oxidative coupling-type chromogen is a chromogen that is converted into a dye by oxidative-coupling of two compounds in the presence of hydrogen peroxide and a peroxidative substance such as peroxidase. Examples of the combinations of the two compounds include combinations of a coupler and an aniline and combinations of a coupler and a phenol.

Examples of the couplers are 4-aminoantipyrine (4-AA) and 3-methyl-2-benzothiazolinone hydrazine. Examples of the aniline include N-(3-sulfopropyl)aniline, N-ethyl-N-(2-hydroxy-3-sulfopropyl)-3-methylaniline (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3-methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-

3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-ethyl-N-(3-methylphenyl)-N'-acetylethylenediamine and N-ethyl-N-(2-hydroxy-3-sulfopropyl)-4-fluoro-3,5-dimethoxyaniline (F-DAOS). Examples of the phenol include phenol, 4-chlorophenol, 3-methylphenol, 3-hydroxy-2,4,6-triiodobenzoic acid (HTIB).

Peroxidase is usually used at a concentration of 1 to 100 kU/L. The chromogen is usually used at a concentration of 0.01 to 10 g/L.

The chromogens used for the determination of reduced coenzyme are, for example, those which are converted into a dye by reduced coenzyme and reduction in the presence of diaphorase or an electron carrier. Examples of the chromogens include 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1) and 2-(4-iodophenyl)-3-(2,4-dinitrophenyl)-5-(2,4-disulfophenyl)-2H-tetrazolium monosodium salt (WST-3).

Diaphorase and the electron carrier are usually used at a concentration of 1 to 100 kU/L. The chromogen is usually used at a concentration of 0.01 to 10 g/L.

Examples of the cyclodextrin or its derivatives are cyclodextrin, dimethylcyclodextrin, trimethylcyclodextrin, hydroxyethylcyclodextrin, hydroxypropylcyclodextrin, carboxymethylcyclodextrin, glycosylcyclodextrin, maltosylcyclodextrin, cyclodextrin sulfate and cyclodextrin polymer, and preferred are hydroxyethylcyclodextrin and hydroxypropylcyclodextrin.

Examples of the cyclodextrin are α-cyclodextrin, β-cyclodextrin and γ-cyclodextrin.

Examples of the dimethylcyclodextrin are dimethyl-α-cyclodextrin, dimethyl-β-cyclodextrin and dimethyl-γ-cyclodextrin.

Examples of the trimethylcyclodextrin are trimethyl-α-cyclodextrin, trimethyl-β-cyclodextrin and trimethyl-γ-cyclodextrin.

Examples of the hydroxyethylcyclodextrin are hydroxyethyl-α-cyclodextrin, hydroxyethyl-β-cyclodextrin and hydroxyethyl-γ-cyclodextrin.

Examples of the hydroxypropylcyclodextrin are hydroxypropyl-α-cyclodextrin, hydroxypropyl-β-cyclodextrin and hydroxypropyl-γ-cyclodextrin.

Examples of the carboxymethylcyclodextrin are carboxymethyl-α-cyclodextrin, carboxymethyl-β-cyclodextrin and carboxymethyl-γ-cyclodextrin.

Examples of the glycosylcyclodextrin are glycosyl-α-cyclodextrin, glycosyl-β-cyclodextrin and glycosyl-γ-cyclodextrin.

Examples of the maltosylcyclodextrin are maltosyl-α-cyclodextrin, maltosyl-β-cyclodextrin and maltosyl-γ-cyclodextrin.

Examples of the cyclodextrin sulfate are α-cyclodextrin sulfate, β-cyclodextrin sulfate and γ-cyclodextrin sulfate.

An example of the cyclodextrin polymer is a β-cyclodextrin polymer. Two or more kinds of cyclodextrin or derivatives thereof can be used in combination.

In the aqueous medium, the concentration of cyclodextrin or its derivative is preferably 0.001 to 5 (w/v) %, more preferably 0.005 to 2.5 (w/v) %, and particularly preferably 0.01 to 1 (w/v) %.

Examples of the albumin include albumin obtained from cow, horse, sheep and human, and bovine serum albumin (BSA) is preferred. Albumin produced by genetic engineering techniques can also be used. Two or more kinds of albumin can be used in combination. In the aqueous medium, the concentration of albumin is preferably 0.001 to 5 (w/v) %, more preferably 0.005 to 2.5 (w/v) %, and particularly preferably 0.01 to 1 (w/v) %.

Examples of the lipoprotein aggregating agents include polyanions such as phosphorus wolframate, dextran sulfate and heparin and salts of divalent metals such as magnesium, calcium and cobalt. In the aqueous medium, the concentration of the lipoprotein aggregating agent is preferably 0.001 to 5 (w/v) % (for each of the polyanion and the metal salt), more preferably 0.005 to 2.5 (w/v) %, and particularly preferably 0.01 to 1 (w/v) %.

Examples of the enzyme activators include anionic surfactants such as bile acids and alkylsulfonates. Examples of the bile acids are cholic acid, deoxycholic acid, taurocholic acid and chenodeoxycholic acid. Examples of the alkylsulfonates are 1-pentasulfonate, 1-hexasulfonate, 1-heptasulfonate and 1-octasulfonate. Examples of the salts of alkylsulfonate are ammonium salt, lithium salt, sodium salt, potassium salt, magnesium salt and calcium salt.

Examples of the stabilizers are ethylenediaminetetraacetic acid (EDTA), sucrose and calcium chloride.

Examples of the antiseptics include sodium azide and antibiotics.

Examples of the interference inhibitors include ascorbate oxidase to inhibit the effect of ascorbic acid and potassium ferrocyanide to inhibit the effect of bilirubin.

Examples of the salts are lithium chloride, lithium sulfate, sodium chloride, sodium sulfate, potassium chloride, potassium sulfate, magnesium chloride, magnesium sulfate, magnesium acetate, ammonium chloride, magnesium sulfate, magnesium nitrate and calcium nitrate.

Certain embodiments of the method for the determination of RLP-C of the present invention are illustrated below.

Method 1

A method which comprises:
(1) carrying out enzymatic reactions in an aqueous medium in the presence of a sample, a phospholipid-hydrolyzing enzyme, surfactant (d1), surfactant (d2), cholesterol esterase and cholesterol oxidase;
(2) measuring the formed hydrogen peroxide; and
(3) determining the concentration of RLP-C in the sample from the value measured in (2) and a previously prepared calibration curve.

Method 2

A method which comprises:
(1) carrying out enzymatic reactions in an aqueous medium in the presence of a sample, a phospholipid-hydrolyzing enzyme, surfactant (d3), surfactant (d4), cholesterol esterase and cholesterol oxidase;
(2) measuring the formed hydrogen peroxide; and
(3) determining the concentration of RLP-C in the sample from the value measured in (2) and a previously prepared calibration curve.

Method 3

A method which comprises:
(1) carrying out enzymatic reactions in an aqueous medium in the presence of a sample, a phospholipid-hydrolyzing enzyme, surfactant (d1), surfactant (d2), cholesterol esterase, oxidized coenzyme and cholesterol dehydrogenase;
(2) measuring the formed reduced coenzyme; and
(3) determining the concentration of RLP-C in the sample from the value measured in (2) and a previously prepared calibration curve.

Method 4

A method which comprises:

(1) carrying out enzymatic reactions in an aqueous medium in the presence of a sample, a phospholipid-hydrolyzing enzyme, surfactant (d3), surfactant (d4), cholesterol esterase, oxidized coenzyme and cholesterol dehydrogenase;

(2) measuring the formed reduced coenzyme; and (3) determining the concentration of RLP-C in the sample from the value measured in (2) and a previously prepared calibration curve.

(Reagent for the Determination of RLP-C)

In one embodiment of the present invention, the reagent for the determination of RLP-C comprises a phospholipid-hydrolyzing enzyme, cholesterol esterase, cholesterol oxidase, and a combination of surfactant (d1) and surfactant (d2) or a combination of surfactant (d3) and surfactant (d4). This reagent may comprise a reagent for the determination of hydrogen peroxide. An example of the reagent for the determination of hydrogen peroxide is a reagent comprising peroxidase and the above-described chromogen which is converted into a dye by hydrogen peroxide and oxidation in the presence of peroxidase.

In another embodiment of the present invention, the reagent for the determination of RLP-C comprises a phospholipid-hydrolyzing enzyme, cholesterol esterase, oxidized coenzyme, cholesterol dehydrogenase, and a combination of surfactant (d1) and surfactant (d2) or a combination of surfactant (d3) and surfactant (d4). This reagent may comprise a reagent for the determination of reduced coenzyme. An example of the reagent for the determination of reduced coenzyme is a reagent comprising diaphorase or an electron carrier and the above-described chromogen which is converted into a dye by reduced coenzyme and reduction in the presence of diaphorase or an electron carrier.

Certain embodiments of the reagent for the determination of RLP-C of the present invention are illustrated below.

Reagent 1

A reagent comprising cholesterol esterase, cholesterol oxidase, surfactant (d1), surfactant (d2) and a reagent for the measurement of hydrogen peroxide Reagent 2

A reagent comprising cholesterol esterase, cholesterol oxidase, surfactant (d3), surfactant (d4) and a reagent for the measurement of hydrogen peroxide Reagent 3

A reagent comprising cholesterol esterase, oxidized coenzyme, cholesterol dehydrogenase, surfactant (d1) and surfactant (d2)

Reagent 4

A reagent comprising cholesterol esterase, oxidized coenzyme, cholesterol dehydrogenase, surfactant (d3) and surfactant (d4)

Reagent 5

A reagent comprising cholesterol esterase, oxidized coenzyme, cholesterol dehydrogenase, surfactant (d1), surfactant (d2) and a reagent for the measurement of reduced coenzyme Reagent 6

A reagent comprising cholesterol esterase, oxidized coenzyme, cholesterol dehydrogenase, surfactant (d3), surfactant (d4) and a reagent for the measurement of reduced coenzyme (Kit for the Determination of RLP-C)

The reagent for the determination of RLP-C of the present invention is preferably preserved, distributed and used in the form of a kit. The kit may be composed of two reagents or three reagents, and preferred is a kit composed of two reagents.

In the kit composed of two reagents (a first reagent and a second reagent), cholesterol esterase, and cholesterol oxidase or cholesterol dehydrogenase may be contained in separate reagents, but are preferably contained in the same reagent, specifically preferably in the second reagent. The phospholipid-hydrolyzing enzyme may be contained in either or both of the first reagent and the second reagent, but is preferably contained in the second reagent.

Surfactant (d1) and surfactant (d2) may be contained in either or both of the first reagent and the second reagent, but surfactant (d1) is preferably contained in the first reagent. Surfactant (d3) and surfactant (d4) may be contained in either or both of the first reagent and the second reagent, but surfactant (d3) is preferably contained in the first reagent.

Oxidized coenzyme is contained in at least one of the first reagent and the second reagent. A reagent for the determination of hydrogen peroxide is contained in at least one of the first reagent and the second reagent, but when the reagent comprises an oxidative coupling-type chromogen, the two compounds thereof are preferably contained in separate reagents, respectively. A reagent for the determination of reduced coenzyme is contained in at least one of the first reagent and the second reagent.

Certain embodiments of the kit for the determination of RLP-C of the present invention are illustrated below.

Kit 1

First Reagent

A reagent comprising surfactant (d1) and a part of a reagent for the determination of hydrogen peroxide Second Reagent A reagent comprising surfactant (d2), a phospholipid-hydrolyzing enzyme, cholesterol esterase, cholesterol oxidase and the remaining part of the reagent for the determination of hydrogen peroxide Kit 2

First Reagent

A reagent comprising surfactant (d3) and a part of a reagent for the determination of hydrogen peroxide Second Reagent A reagent comprising surfactant (d4), a phospholipid-hydrolyzing enzyme, cholesterol esterase, cholesterol oxidase and the remaining part of the reagent for the determination of hydrogen peroxide Kit 3

First Reagent

A reagent comprising surfactant (d1)

Second Reagent

A reagent comprising surfactant (d2), a phospholipid-hydrolyzing enzyme, cholesterol esterase, oxidized coenzyme and cholesterol dehydrogenase Kit 4

First Reagent

A reagent comprising surfactant (d3)

Second Reagent

A reagent comprising surfactant (d4), a phospholipid-hydrolyzing enzyme, cholesterol esterase, oxidized coenzyme and cholesterol dehydrogenase Kit 5

First Reagent

A reagent comprising surfactant (d1)

Second Reagent

A reagent comprising surfactant (d2), a phospholipid-hydrolyzing enzyme, cholesterol esterase, oxidized coenzyme, cholesterol dehydrogenase and a reagent for the determination of reduced coenzyme Kit 6
First Reagent
A reagent comprising surfactant (d3)
Second Reagent
A reagent comprising surfactant (d4), a phospholipid-hydrolyzing enzyme, cholesterol esterase, oxidized coenzyme, cholesterol dehydrogenase and a reagent for the determination of reduced coenzyme The reagent and the kit for the determination of RLP-C of the present invention can be used for the determination of RLP-C in a sample.

The phospholipid-hydrolyzing enzyme, cholesterol esterase, cholesterol oxidase, oxidized coenzyme, cholesterol dehydrogenase, surfactant (d1), surfactant (d2), surfactant (d3), surfactant (d4), the reagent for the determination of hydrogen peroxide and the reagent for the determination of reduced coenzyme which are described in the above description of the method for the determination of RLP-C can be used as the components of the reagent and the kit for the determination of RLP-C of the present invention.

The reagent and the kit for the determination of RLP-C of the present invention may comprise, according to need, the above-described aqueous medium, cyclodextrin or its derivative, albumin, lipoprotein aggregating agent, enzyme activator, stabilizer, antiseptic, interference inhibitor and various salts for solubilizing proteins such as globulin in a biological sample.

The reagent and the kit for the determination of RLP-C of the present invention comprise enzymes and two kinds of surfactants in amounts that give the concentrations described in the above description of the method for the determination of RLP-C in an aqueous medium.

Certain embodiments of the present invention are illustrated in the following examples, which are not to be construed as limiting the scope of the invention.
Reagents and apparatus from the following manufacturers were used in the examples.
MOPS (Good's buffer, Dojindo Laboratories), TOOS [Trinder's reagent (oxidative coupling-type chromogen), Dojindo Laboratories], 4-aminoantipyrine (Nakalai Tesque, Inc.), sodium sulfate (Wako Pure Chemical Industries, Ltd.), Plonon B-208 {POE·POB copolymer [surfactant (d1)], NOF Corporation}, Plonon B-204 {POE·POB copolymer [surfactant (d1)], NOF Corporation}, Wondersurf RL-100 {POE·POP alkyl ether [surfactant (d2)], Aoki Oil Industrial Co., Ltd.}, Wondersurf ID-70 {POE·POP short-chain branched alkyl ether [surfactant (d2)], Aoki Oil Industrial Co., Ltd.}, Wondersurf ID-90 {POE·POP short-chain branched alkyl ether [surfactant (d2)], Aoki Oil Industrial Co., Ltd.}, Emulgen L-40 {POE·POP alkylaryl ether [surfactant (d2)], Kao Corporation}, Pluronic F-108 (POE·POP copolymer, Adeka Corporation), phospholipase D (Asahi Kasei Corporation), cholesterol oxidase (CHOD, Kyowa Hakko Kogyo Co., Ltd.), cholesterol esterase (CHER, Toyobo Co., Ltd.), peroxidase (POD, Toyobo Co., Ltd.) and ascorbate oxidase (AOD, Asahi Kasei Corporation).

EXAMPLE 1

Kit for the Determination of RLP-C

A kit for the determination of RLP-C comprising the following first reagent and second reagent was prepared.

| First reagent | |
|---|---|
| MOPS (pH 6.8) | 20 mmol/L |
| TOOS | 0.3 g/L |
| Sodium sulfate | 2 g/L |
| Plonon B-208 | 8 g/L |
| Wondersurf RL-100 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Wondersurf RL-100 | 1 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

EXAMPLE 2

Kit for the Determination of RLP-C

A kit for the determination of RLP-C comprising the following first reagent and second reagent was prepared.

| First reagent | |
|---|---|
| MOPS (pH 6.8) | 20 mmol/L |
| TOOS | 0.3 g/L |
| Sodium sulfate | 2 g/L |
| Plonon B-204 | 8 g/L |
| Wondersurf ID-70 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Wondersurf ID-70 | 1 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

EXAMPLE 3

Kit for the Determination of RLP-C

A kit for the determination of RLP-C comprising the following first reagent and second reagent was prepared.

| First reagent | |
|---|---|
| MOPS (pH 6.8) | 20 mmol/L |
| TOOS | 0.3 g/L |
| Sodium sulfate | 2 g/L |
| Plonon B-208 | 8 g/L |
| Emulgen L-40 | 2 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Emulgen L-40 | 3 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

COMPARATIVE EXAMPLE 1

Kit for the Determination of RLP-C

A kit for the determination of RLP-C comprising the following first reagent and second reagent was prepared. This formulation is the one described in Example 1 of Japanese Published Unexamined Patent Application No. 231597/01.

| First reagent | |
|---|---|
| MOPS (pH 6.8) | 20 mmol/L |
| TOOS | 0.3 g/L |
| Sodium sulfate | 2 g/L |
| Pluronic F-108 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Emulgen L-40 | 2 g/L |
| Peroxidase | 10 U/mL |
| Cholesterol esterase (CHER) | 1 U/mL |
| Cholesterol oxidase (CHOD) | 2 U/mL |
| Phospholipase D | 5 U/mL |

EXAMPLE 4

Determination of RLP-C

Determination of RLP-C in fresh human serum (64 samples) was carried out on Hitachi-7170 autoanalyzer using the kit of Example 1 in the following manner.

(1) Preparation of a Calibration Curve

A standard serum solution found to have an RLP-C concentration of 32.4 mg/dL by measurement using RLP-cholesterol "JIMRO" II (JIMRO Co., Ltd.) was used as a standard solution, and serum dilutions prepared by appropriately diluting the standard serum solution were used as samples for preparation of a calibration curve.

A calibration curve was prepared by determining the concentration of RLP-C in each of the serum dilutions on Hitachi-7170 autoanalyzer using the kit of Example 1 as a measurement kit in the following manner.

To a reaction cell were added a serum dilution (3.8 µL) and the first reagent (0.18 mL), and the resulting mixture was incubated at 37° C. for 5 minutes. The absorbance of the reaction solution (E1) was measured at a main wavelength of 600 nm and a sub-wavelength of 700 nm (photometric point: 16). Then, the second reagent (0.06 mL) previously heated to 37° C. was added to the reaction solution, followed by further incubation at 37° C. for 5 minutes, and the absorbance of the reaction solution (E2) was measured at a main wavelength of 600 nm and a sub-wavelength of 700 nm (photometric point: 32). A calibration curve was prepared based on the relationship between the change in absorbance by the reaction (E2-E1) and the RLP-C concentration of serum dilutions.

(2) Determination of RLP-C in Fresh Human Serum (64 Samples)

Reaction was carried out in the same manner as in (1) using 64 fresh human serum samples in place of the standard serum solution, and the RLP-C concentration of each sample was determined from the absorbance of the reaction solution after the reaction and the calibration curve prepared in (1).

EXAMPLE 5

Determination of RLP-C

The RLP-C concentration of each of the fresh human serum samples (64 samples) used in the determination of Example 4 was determined on Hitachi-7170 autoanalyzer in the same manner as in Example 4, except that the kit of Example 2 was used in place of the kit of Example 1.

EXAMPLE 6

Determination of RLP-C

The RLP-C concentration of each of the fresh human serum samples (64 samples) used in the determination of Example 4 was determined on Hitachi-7170 autoanalyzer in the same manner as in Example 4, except that the kit of Example 3 was used in place of the kit of Example 1.

COMPARATIVE EXAMPLE 2

Determination of RLP-C

The RLP-C concentration of each of the fresh human serum samples (64 samples) used in the determination of Example 4 was determined on Hitachi-7170 autoanalyzer in the same manner as in Example 4, except that the kit of Comparative Example 1 was used in place of the kit of Example 1.

TEST EXAMPLE 1

Correlation with Measurement Using RLP-cholesterol "JIMRO" II (JIMRO Co., Ltd.)

The RLP-C concentration of each of the above fresh human serum samples (64 samples) was determined using RLP-cholesterol "JIMRO" II (JIMRO Co., Ltd.).

Figure 2:
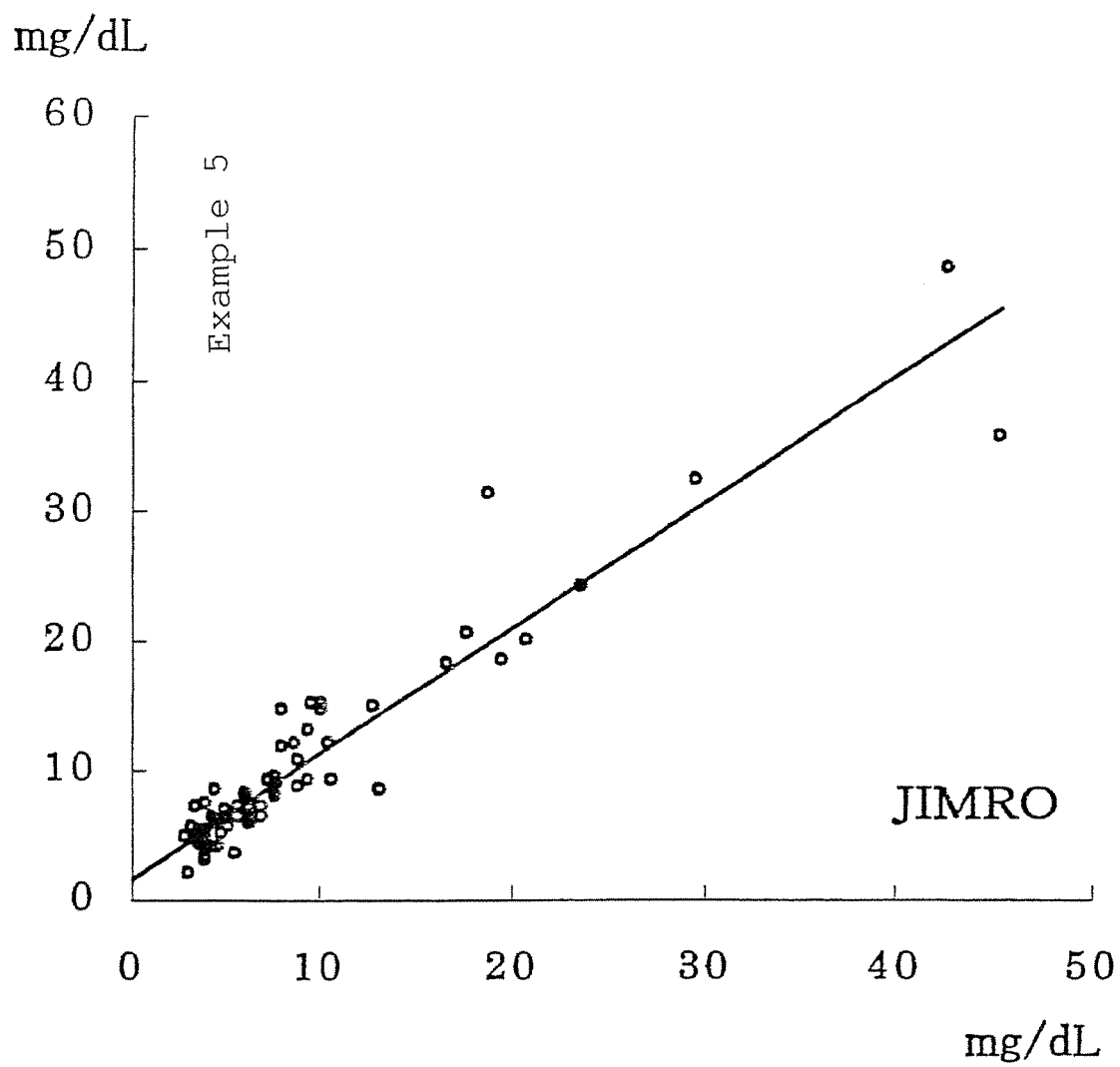
FIG. 2 is a graph showing the correlation between the determination method using RLP-cholesterol "JIMRO" II (JIMRO Co., Ltd.) and the determination method of Example 5.
Figure 3:
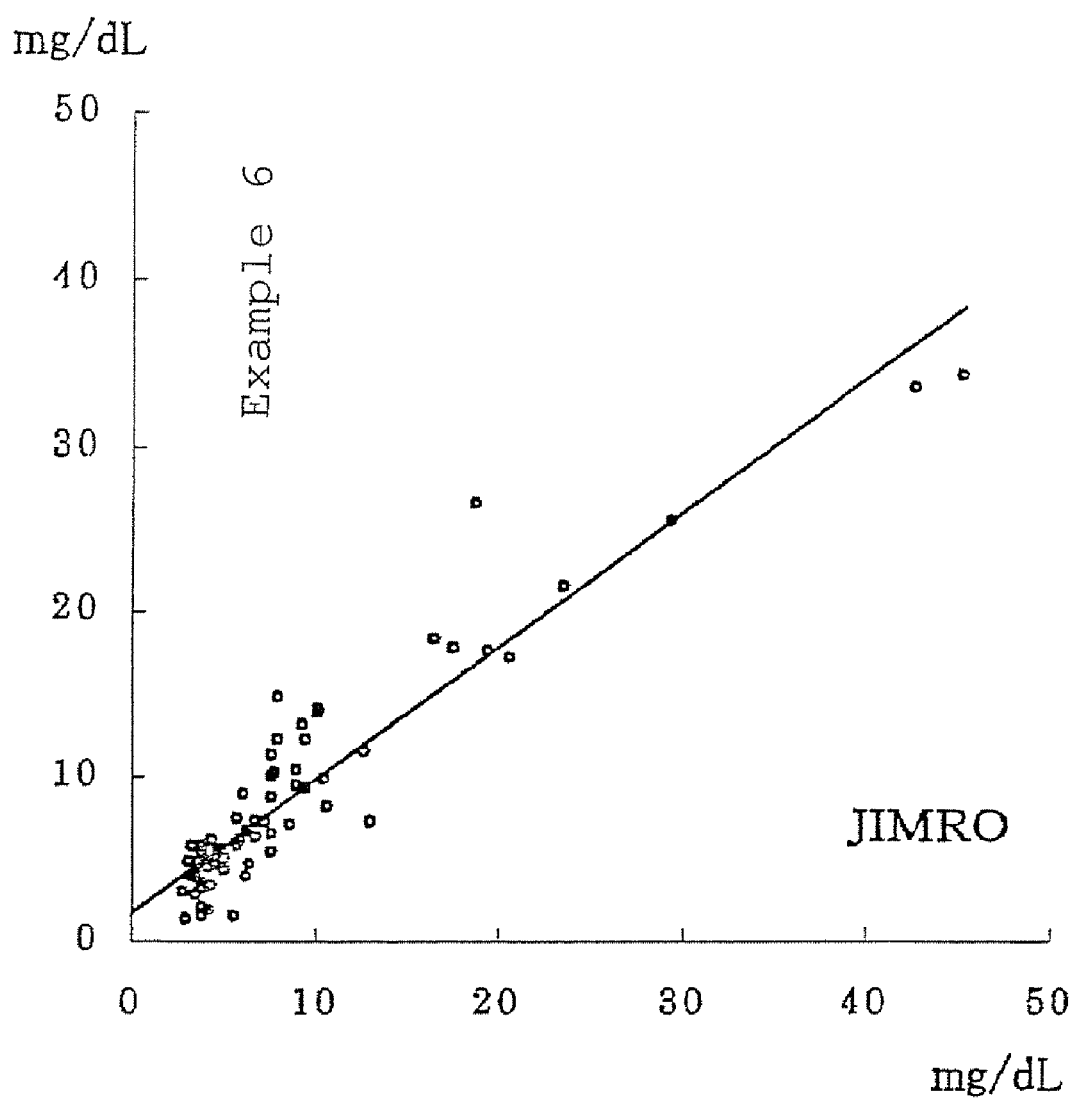
FIG. 3 is a graph showing the correlation between the determination method using RLP-cholesterol "JIMRO" II (JIMRO Co., Ltd.) and the determination method of Example 6.
Figure 4:
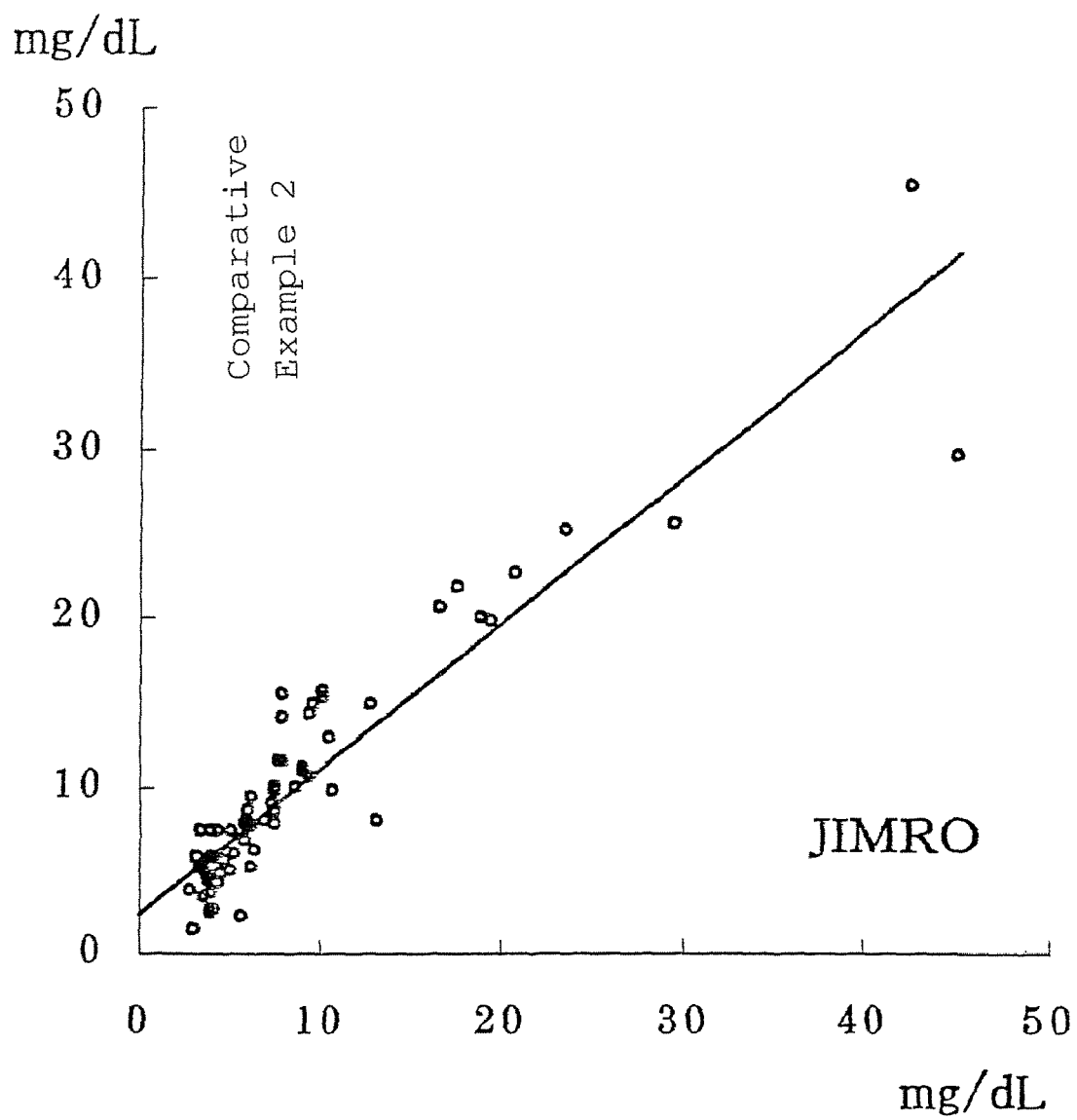
FIG. 4 is a graph showing the correlation between the determination method using RLP-cholesterol "JIMRO" II (JIMRO Co., Ltd.) and the determination method of Comparative Example 2.

The correlation between each of the determination methods of Examples 4 to 6 and Comparative Example 2 and the determination method using RLP-cholesterol "JIMRO" II was evaluated by correlation coefficient. The results are shown in Table 11. Graphs showing the correlation are given in FIG. 1 to FIG. 4.

TABLE 11

| Determination method | Correlation coefficient in the correlation with the determination method using RLP-cholesterol "JIMRO" II |
|---|---|
| Example 4 | 0.9513 |
| Example 5 | 0.9447 |
| Example 6 | 0.9319 |
| Comparative Example 2 | 0.9253 |

As shown in Table 11, it was revealed that the methods according to the present invention have a good correlation with the determination method using RLP-cholesterol "JIMRO" II compared with Comparative Example 2 (determination using the kit described in Example 1 of Japanese Published Unexamined Patent Application No. 231597/01).

TEST EXAMPLE 2

Determination of RLP-C in Type III Hyperlipidemia Samples

The RLP-C concentration of serum samples from patients with type III hyperlipidemia was determined using RLP-cholesterol "JIMRO" II (JIMRO Co., Ltd.) and the kits of Examples 1 to 3 and Comparative Example 1. A standard serum solution found to have an RLP-C concentration of 32.4 mg/dL by measurement using RLP-cholesterol "JIMRO" II (JIMRO Co., Ltd.) was used as a standard solution, and serum dilutions prepared by appropriately diluting the standard serum solution were used as samples for preparation of a calibration curve. The results are shown in Table 12.

TABLE 12

| Kit | RLP-C concentration of type III hyperlipidemia samples (mg/dL) |
| --- | --- |
| Example 1 | 28.6 |
| Example 2 | 31.4 |
| Example 3 | 26.5 |
| Comparative Example 1 | 20.0 |
| JIMRO | 18.8 |

It is known that the level of VLDL remnant is especially high in the serum of patients with type III hyperlipidemia. Therefore, it can be seen from the results in Table 12 that the reactivity to cholesterol in VLDL remnant is improved in the determination methods according to the present invention compared with the method using the kit of Comparative Example 1 (the kit described in Example 1 of Japanese Published Unexamined Patent Application No. 231597/01). It can also be seen that the reactivity to RLP-C in the determination methods according to the present invention is higher than that in the method using RLP-cholesterol "JIMRO" II.

EXAMPLE 7

Kit for the Determination of RLP-C

A kit for the determination of RLP-C comprising the following first reagent and second reagent was prepared.

| First reagent | |
| --- | --- |
| MOPS (pH 6.8) | 20 mmol/L |
| TOOS | 0.3 g/L |
| Sodium sulfate | 2 g/L |
| Plonon B-208 | 8 g/L |
| Emulgen L-40 | 1 g/L |
| Wondersurf ID-70 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Wondersurf ID-70 | 1 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

EXAMPLE 8

Kit for the Determination of RLP-C

A kit for the determination of RLP-C comprising the following first reagent and second reagent was prepared.

| First reagent | |
| --- | --- |
| MOPS (pH 6.8) | 20 mmol/L |
| TOOS | 0.3 g/L |
| Sodium sulfate | 2 g/L |
| Plonon B-208 | 8 g/L |
| Emulgen L-40 | 1 g/L |
| Wondersurf ID-70 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Wondersurf ID-70 | 1 g/L |
| Emulgen L-40 | 1 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

EXAMPLE 9

Kit for the Determination of RLP-C

A kit for the determination of RLP-C comprising the following first reagent and second reagent was prepared.

| First reagent | |
| --- | --- |
| MOPS (pH 6.8) | 20 mmol/L |
| TOOS | 0.3 g/L |
| Sodium sulfate | 2 g/L |
| Plonon B-208 | 8 g/L |
| Emulgen L-40 | 1 g/L |
| Wondersurf ID-90 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Wondersurf ID-90 | 1 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

EXAMPLE 10

Kit for the Determination of RLP-C

A kit for the determination of RLP-C comprising the following first reagent and second reagent was prepared.

| First reagent | |
| --- | --- |
| MOPS (pH 6.8) | 20 mmol/L |
| TOOS | 0.3 g/L |

-continued

| | |
|---|---|
| Sodium sulfate | 2 g/L |
| Plonon B-208 | 8 g/L |
| Emulgen L-40 | 1 g/L |
| Wondersurf ID-90 | 1 g/L |
| Peroxidase (POD) | 10 U/mL |
| Ascorbate oxidase (AOD) | 2 U/mL |
| Second reagent | |
| MOPS (pH 6.8) | 20 mmol/L |
| 4-Aminoantipyrine | 0.5 g/L |
| Wondersurf ID-90 | 1 g/L |
| Emulgen L-40 | 1 g/L |
| Peroxidase | 10 U/mL |
| Cholesterol esterase (CHER) | 1 U/mL |
| Cholesterol oxidase (CHOD) | 3 U/mL |
| Phospholipase D | 5 U/mL |

EXAMPLE 11

Determination of RLP-C

The same procedure as in Example 4 was carried out, except that the kit of Example 7 was used as the determination kit in place of the kit of Example 1 and 35 fresh human serum samples were used as the samples in place of the 64 fresh human serum samples used in Examples 5 to 8. The RLP-C concentration of each of the 35 samples was determined on Hitachi-7170 autoanalyzer.

EXAMPLE 12

Determination of RLP-C

The RLP-C concentration of each of the fresh human serum samples (35 samples) was determined on Hitachi-7170 autoanalyzer in the same manner as in Example 11, except that the kit of Example 8 was used in place of the kit of Example 7.

EXAMPLE 13

Determination of RLP-C

The RLP-C concentration of each of the fresh human serum samples (35 samples) was determined on Hitachi-7170 autoanalyzer in the same manner as in Example 11, except that the kit of Example 9 was used in place of the kit of Example 7.

EXAMPLE 14

Determination of RLP-C

The RLP-C concentration of each of the fresh human serum samples (35 samples) was determined on Hitachi-7170 autoanalyzer in the same manner as in Example 11, except that the kit of Example 10 was used in place of the kit of Example 7.

TEST EXAMPLE 3

Correlation with Measurement Using RLP-cholesterol "JIMRO" II (JIMRO Co., Ltd.)

The RLP-C concentration of each of the fresh human serum samples (35 samples) used in Examples 11 to 14 was determined using RLP-cholesterol "JIMRO" II (JIMRO Co., Ltd.).

Figure 5:
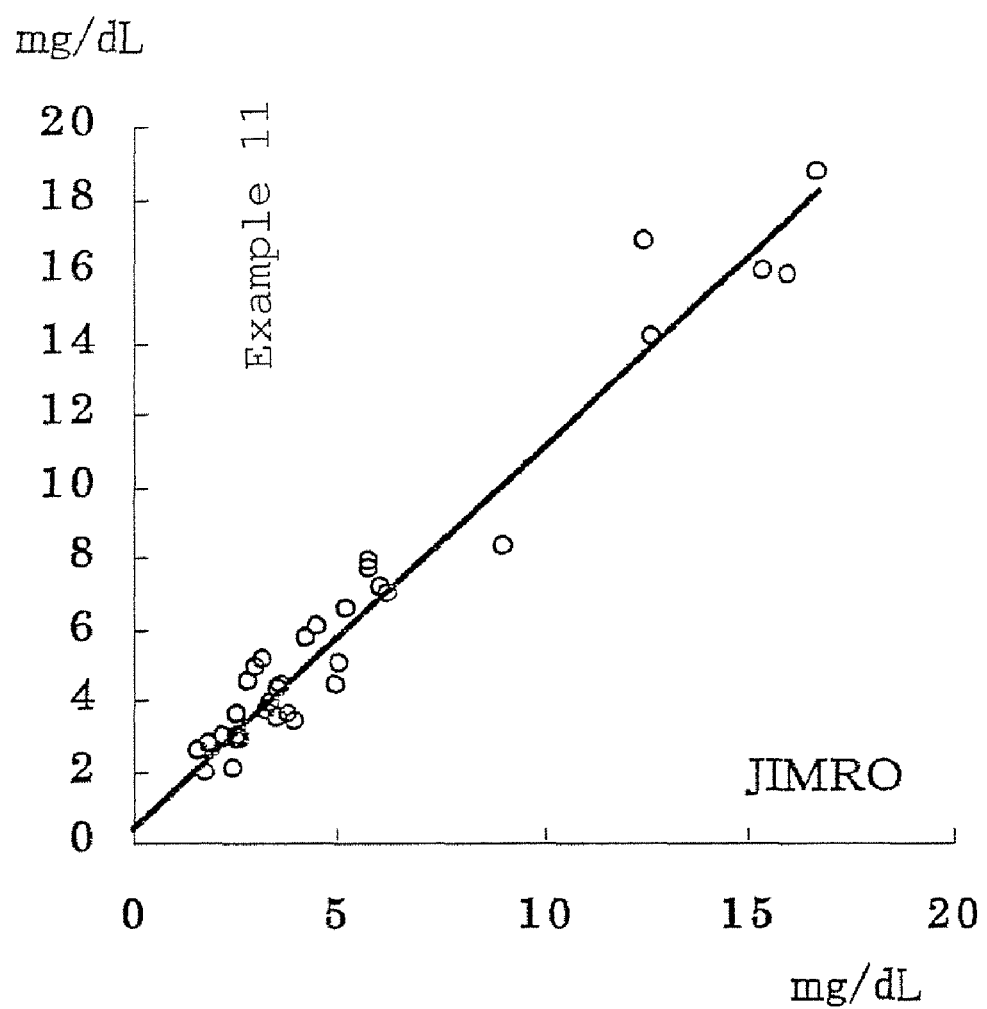
FIG. 5 is a graph showing the correlation between the determination method using RLP-cholesterol "JIMRO" II (JIMRO Co., Ltd.) and the determination method of Example 11.
Figure 6:
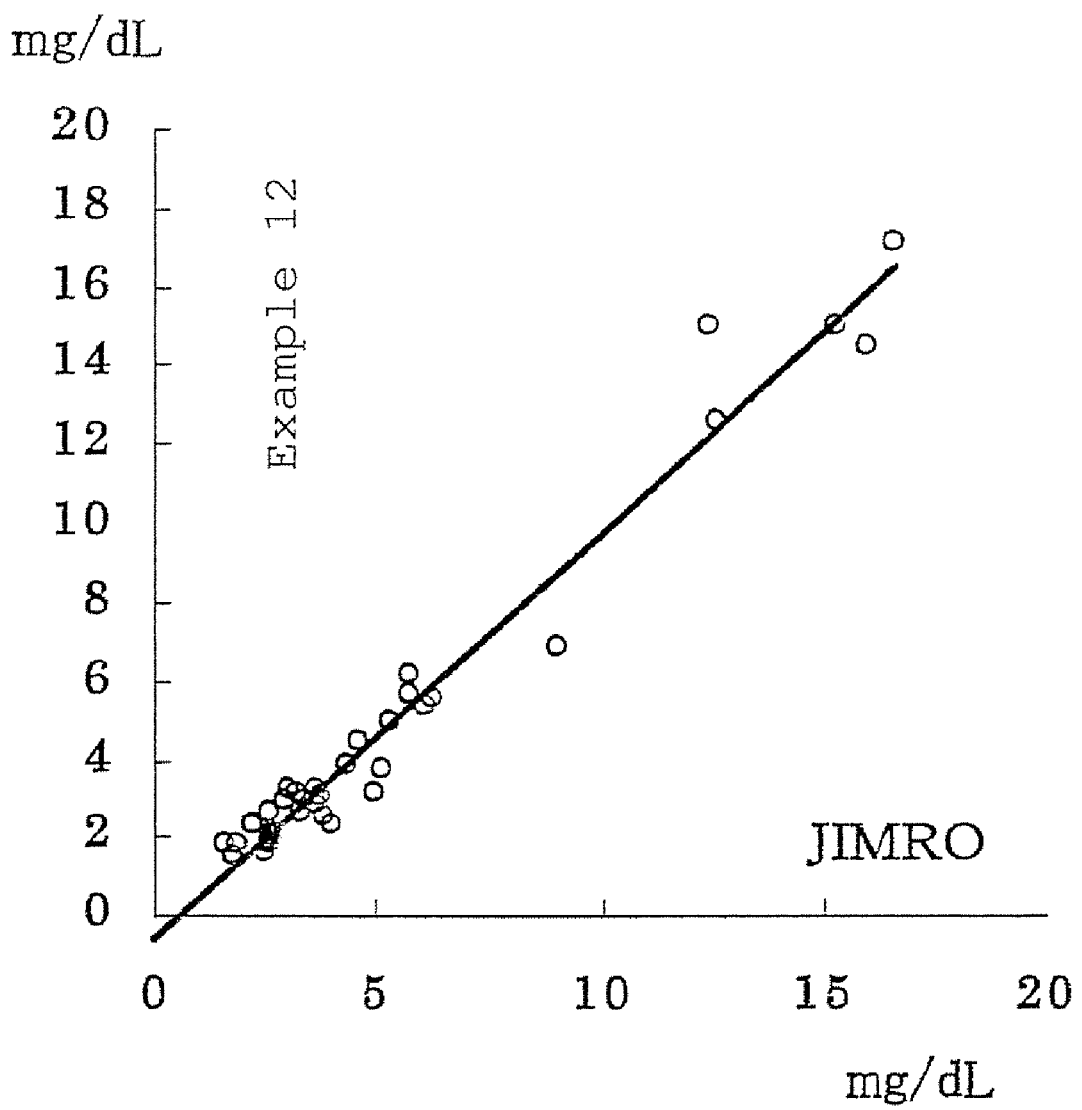
FIG. 6 is a graph showing the correlation between the determination method using RLP-cholesterol "JIMRO" II (JIMRO Co., Ltd.) and the determination method of Example 12.
Figure 7:
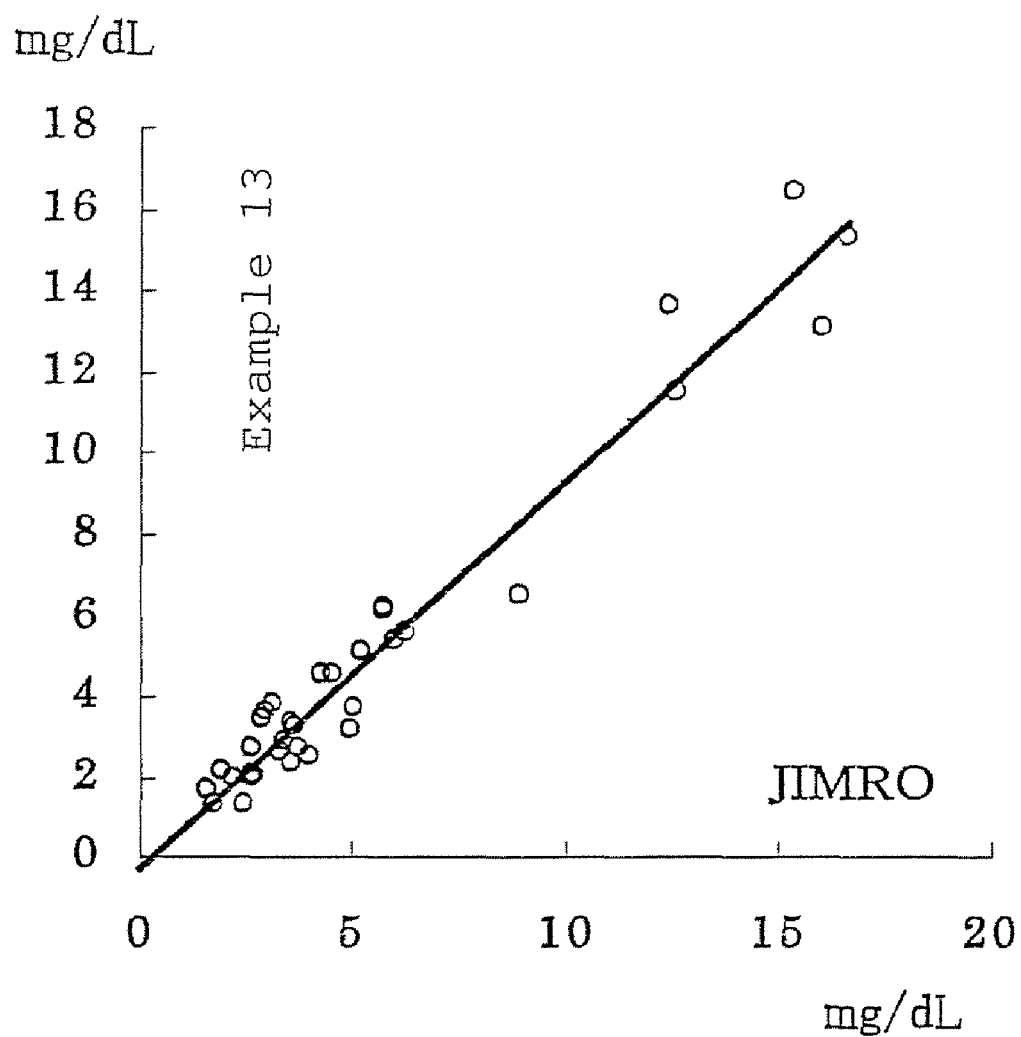
FIG. 7 is a graph showing the correlation between the determination method using RLP-cholesterol "JIMRO" II (JIMRO Co., Ltd.) and the determination method of Example 13.
Figure 8:
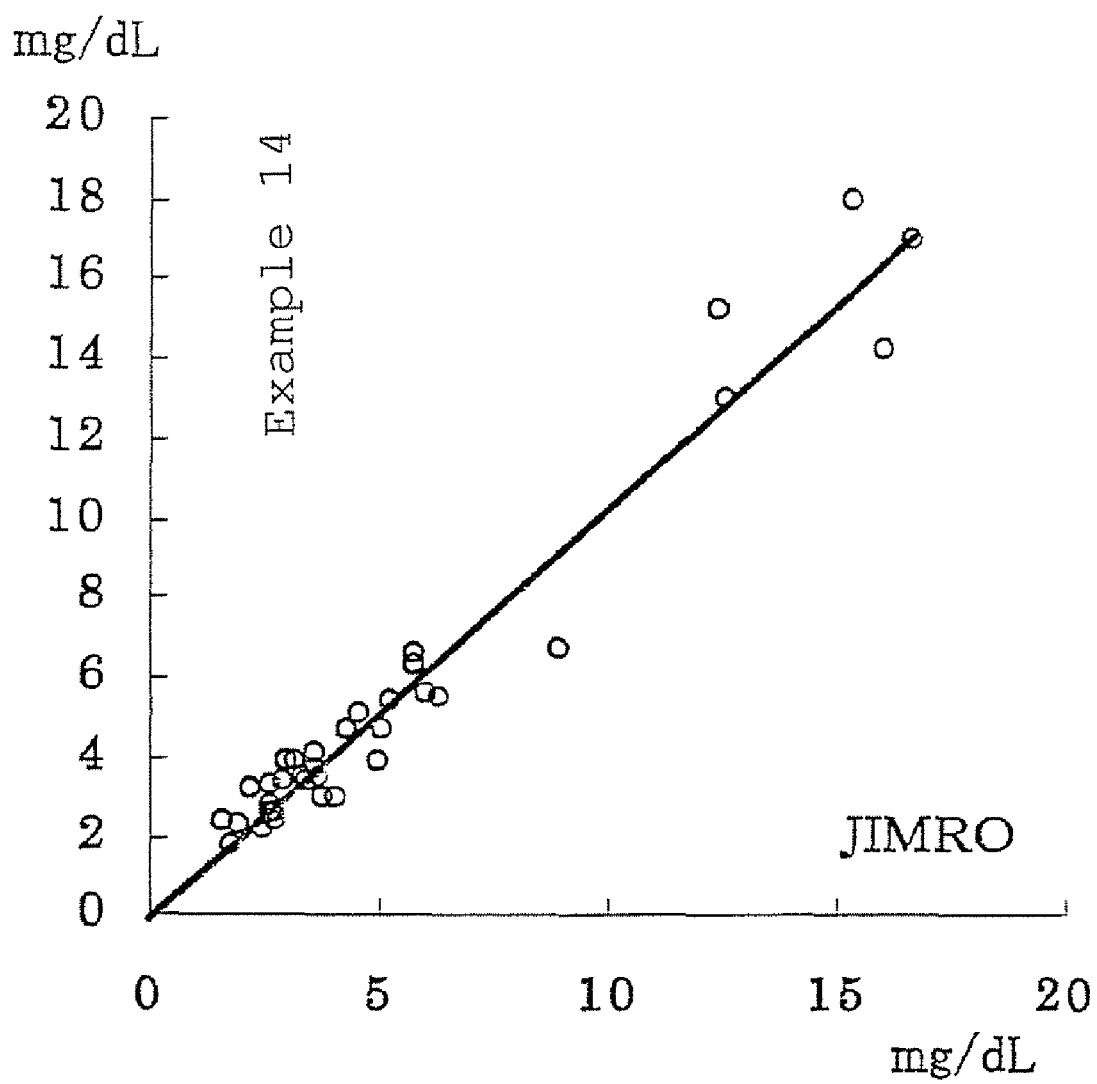
FIG. 8 is a graph showing the correlation between the determination method using RLP-cholesterol "JIMRO" II (JIMRO Co., Ltd.) and the determination method of Example 14.

The correlation between each of the determination methods of Examples 11 to 14 and the determination method using RLP-cholesterol "JIMRO" II was evaluated by correlation coefficient. The results are shown in Table 13. Graphs showing the correlation are given in FIG. 5 to FIG. 8.

TABLE 13

| Determination method | Correlation coefficient in the correlation with the determination method using RLP-cholesterol "JIMRO" II |
|---|---|
| Example 11 | 0.9764 |
| Example 12 | 0.9826 |
| Example 13 | 0.9756 |
| Example 14 | 0.9745 |

As shown in Table 13, a good correlation was also observed between the methods using the kits comprising two kinds of surfactants as surfactant (d2) and the determination method using RLP-cholesterol "JIMRO" II. From the comparison with the results on Examples 4 to 6 shown in Table 11, it was revealed that the determination using the kits comprising two kinds of surfactants (d2) showed a better correlation with the determination method using RLP-cholesterol "JIMRO" II than did the determination using the kits comprising one kind of surfactant (d2).

Industrial Applicability

The present invention provides a method, a reagent and a kit for the quantitative determination of RLP-C which are useful for diagnosis of arteriosclerotic diseases.

The invention claimed is:

1. A method for quantitatively determining cholesterol in remnant-like particles in a sample, which comprises:
   obtaining an aqueous medium containing the sample, a phospholipid-hydrolyzing enzyme, a polyoxyethylene-polyoxybutylene copolymer, and one or more surfactants selected from the group consisting of a polyoxyethylene-polyoxypropylene alkylaryl ether, a polyoxyethylene-polyoxypropylene alkyl ether and a polyoxyethylene-polyoxypropylene short-chain branched alkyl ether;
   reacting a combination of cholesterol esterase and cholesterol oxidase or a combination of cholesterol esterase, oxidized coenzyme and cholesterol dehydrogenase with cholesterol in remnant-like particles in the sample in the aqueous medium to form hydrogen peroxide or reduced coenzyme; and
   determining an amount of the formed hydrogen peroxide or reduced coenzyme.

2. The method according to claim 1, wherein hydrogen peroxide is determined by reacting the formed hydrogen peroxide with an oxidative coloring-type chromogen in the presence of peroxidase and determining the formed dye.

3. The method according to claim 1, wherein the determination of reduced coenzyme is carried out by measuring the absorbance of the reaction solution.

4. The method according to claim 1, wherein the reduced coenzyme is determined by reacting formed reduced coenzyme with a reductive coloring-type chromogen and determining the formed dye.

5. The method according to any of claim 1 to 4, wherein the polyoxyethylene-polyoxybutylene copolymer is a surfactant represented by general formula (I):

$$RO-(C_2H_4O)_A-(C_4H_8O)_B-(C_2H_4O)_C-H \qquad (I)$$

(wherein A, B and C, which may be the same or different, each represent an integer of 1 to 200; and R represents a hydrogen atom, or straight-chain or branched alkyl).

6. The method according to any of claim 1 to 4, wherein the phospholipid-hydrolyzing enzyme is phospholipase D, phospholipase C or phospholipase A2.

7. The method according to claim 5, wherein the phospholipid-hydrolyzing enzyme is phospholipase D, phospholipase C or phospholipase A2.

* * * * *